US005780024A

United States Patent [19]

Brown et al.

[11] Patent Number: 5,780,024

[45] Date of Patent: Jul. 14, 1998

[54] SUPEROXIDE DISMUTASE/TETANUS TOXIN FRAGMENT C HYBRID PROTEIN

[75] Inventors: Robert H. Brown, Needham, Mass.; Paul S. Fishman, Baltimore, Md.; Jonathan W. Francis, Mansfield; Betsy A. Hosler, Melrose, both of Mass.

[73] Assignees: The General Hospital Corp., Boston, Mass.; University of Maryland at Baltimore, Baltimore, Md.

[21] Appl. No.: 668,381

[22] Filed: Jun. 21, 1996

[51] Int. Cl.[6] .......................... A61K 38/44; C12N 15/00; C12N 9/02

[52] U.S. Cl. ...................... 424/94.4; 435/172.3; 435/189

[58] Field of Search .......................... 424/94.4; 435/69.1, 435/172.3, 189, 192, 320.1, 94.4; 514/12; 530/350; 536/23.2, 23.4

[56] References Cited

U.S. PATENT DOCUMENTS 5,171,680 12/1992 Mullenbach et al. .................. 435/189

OTHER PUBLICATIONS

Inouye et al. (1994) J. Biochem 115: 507–515 "Dissociation of Dimer of Bovine Erythrocyte Cu, Zn Superoxide Dismutase . . . ".

Beckman et al., "Superoxide Dismutase and Catalase Conjugated to Polyethylene Glycol Increases Endothelial enzyme Activity and Oxidant Resistance," *J. Biol. Chem.* 263:6884–6892 (1988).

Beaude et al., "Retrograde axonal transport of an exogenous enzyme covalently linked to B–IIb fragment of tetanus toxin," *Biochem J.* 271:87–91 (1990).

Bizzini et al., "An Antigenic Polypeptide Fragment Isolated From Tetanus Toxin: Chemical Characterization, Binding to Gangliosides and . . . Various Neuron Systems," *J. Neurochem.* 28:529–542 (1977).

Bizzini et al., "Use of the B–IIb Tetanus Toxin Derived Fragment as a Specific Neuropharmacological Transport Agent," *Brain Research* 193:221–227 (1980).

Coyle et al., "Oxidative Stress, Glutamate, and Neurodegenerative Disorders," *Science* 262:689–694 (1993).

Dobrenis et al., "Neuronal lysosomal enzyme replacement using fragment C of tetanus toxin," *Proc. Natl. Acad. Sci. USA* 89:2297–2301 (1992).

Eisel et al., "Tetanus toxin: primary structure, expression in *E. coli*, and homology with botulinum toxins," *The EMBO Journal* 5:2495–2502 (1986).

Fairweather et al., "The complete nucleotide sequence of tetanus toxin," *Nucleic Acids Research* 14:7809–7812 (1986).

Fairweather et al., "Cloning, Nucleotide Sequencing, and Expression of Tetanus Toxin Fragment C in *Escherichia coli* ," *J. Bacteriology* 165:21–27 (1986).

Fishman et al., "Enhanced CNS uptake of systemically administered proteins through conjugation with tetanus C–fragment," *J. Neurological Sciences* 98:311–325 (1990).

Habermann et al., "Distribution of $^{125}$I–Tetanus Toxin and $^{125}$I–Toxoid in Rats with Generalized Tetanus, as Influenced by Antitoxin," *Naunyn–Schmiedeberg's Arch. Pharmacol.* 276:327–340 (1973).

Hallewell et al., "Genetically Engineered Polymers of Human CuZn Superoxide Dismutase," *J. Biol. Chem.* 264:5260–5268 (1989).

Halpern et al., "Cloning and Expression of Functional Fragment C of Tetanus Toxin," *Infection and Immunity* 58:1004–1009 (1990).

Inoue et al., "Expression of a Hybrid Cu/Zn–type Superoxide Dismutase Which Has High Affinity for Heparin–like Proteoglycans on Vascular Endothelial Cells," *J. Biol. Chem.* 266:16409–16414 (1991).

Inoue et al., "Targeting Sod By Gene And Protein Engineering And Inhibition of Oxidative Stress In Various Diseases," *Antioxidants in Therapy and Preventive Medicine* (Emerit, ed.) Plenum Press, New York 5–12 (1990).

Michelson et al., "Cell penetration by exogenous superoxide dismutase," *Acta Physiol Scand.* 492:67–80 (1980).

Morris et al., "Interaction of Fragments B and C of Tetanus Toxin with Neural and Thyroid Membranes and with Gangliosides," *J. Biol. Chem.* 255:6071–6076 (1980).

Olanow, "A radical hypothesis for neurodegeneration," *TINS* 16:439–443 (1993).

Rosen et al., "Mutations in Cu/Zn superoxide dismutase gene are associated with familial amyotrophic lateral sclerosis," *Nature* 362:59–62 (1993).

Sherman et al., "Nucleotide sequence and expression of human chromosome 21–encoded superoxide dismutase mRNA," *Proc. Natl. Acad. Sci. USA* 80:5465–5469 (1983).

Takeda et al., "Albumin–binding superoxide dismutase with a prolonged half–life reduces reperfusion brain injury," *Inhibition of Ischemic Brain Damage by Sod* H1708–H1715 (1993).

Turrens et al., "Protection against Oxygen Toxicity by Intravenous Injection of Liposome–entrapped Catalase and Superoxide Dismutase," *J. Clin. Invest.* 73:87–95 (1984).

Weller et al., "Quantitative Comparison Between Tetanus Toxin, Some Fragments and Toxoid for Binding and Axonal Transport in the Rat," *Toxicon* 24:1055–1063 (1986).

*Primary Examiner*—Robert A. Wax
*Assistant Examiner*—Einar Stole
*Attorney, Agent, or Firm*—Fish & Richardson P.C.

[57] ABSTRACT

Disclosed is a 68 kD recombinant hybrid protein comprising an enzymatically active Cu/Zn superoxide dismutase ("SOD-1") moiety and a tetanus toxin fragment C ("TTC") moiety, wherein the TTC moiety selectively delivers the hybrid protein into neurons, and the SOD-1 moiety retains substantial enzymatic activity, following neuronal uptake. Also disclosed are a DNA expression vector encoding the hybrid protein.

7 Claims, 8 Drawing Sheets

SUPEROXIDE DISMUTASE/TETANUS TOXIN FRAGMENT C HYBRID PROTEIN

STATEMENT AS TO FEDERALLY SPONSORED RESEARCH

Work on this invention was supported, in part, with funds from the United States government (NIH grants NS31248-01 and 1PO1NS31248). The government therefore has certain rights in the invention.

CROSS REFERENCE TO RELATED APPLICATION

This application claims benefit from provisional application Ser. No. 60/000,473, filed Jun. 23, 1995, and is a continuation-in-part of application Ser. No. 60/000,473.

BACKGROUND OF THE INVENTION

Oxidative stress (or oxidative damage) has been implicated in various neurological diseases and disorders, including stroke, brain hypoxia-reperfusion, trauma, epilepsy, and age related degenerative disorders of the brain, such as Parkinson's disease, Huntington's disease, and amyotrophic lateral sclerosis (Coyle, J. T. et al., (1993) *Science* 262, 689–695; Olanow, C. W. (1993) *Trends Neurosci.* 16, 439–444). Oxidative stress is largely a matter of cellular damage caused by oxygen-derived free radicals, i.e., superoxide radicals and hydroxyl radicals. An important biological mechanism for coping with oxygen-derived free radicals is the activity of superoxide dismutase enzymes, which "scavenge" superoxide radicals (by dismutating them to form hydrogen peroxide, which is eliminated by catalase). Cu/Zn superoxide dismutase ("SOD-1") is a 32 kD homodimeric enzyme. Mutations in human SOD-1 have been associated with the inherited form of amyotrophic lateral sclerosis ("FALS") (Rosen et al. (1993) *Nature* 362: 59–62).

The therapeutic use of SOD-1 presents at least two practical difficulties. First, human SOD-1 is an intracellular, cytosolic enzyme with an isoelectric point of 4.5, and it does not readily cross cell membranes (Michelson et al. (1980) *Acta Physiol. Scand.* 492 (Suppl): 67–80). Second, the molecular weight of SOD-1 is well below the renal glomerular filtration cutoff. This results in rapid clearance of exogenous SOD-1 from the circulation (Inoue et al. (1990) in *Antioxidants in Therapy and Preventive Medicine* (Emerit et al., eds), pp. 5–12, Plenum Press, New York). In efforts to overcome these limitations, SOD-1 has been entrapped in liposomes (Turrens (1984) *J. Clin. Invest.* 73: 87–95); conjugated to albumin (Takeda et al. (1993) *Am. J. Physiol.* 264: H1708–H1715); conjugated to polyethylene glycol (Beckman et al. (1988) *J. Biol. Chem.* 263: 6884–6892); and expressed as a fusion protein comprising a heparin-binding peptide (Inoue et al. (1991) *J. Biol. Chem.* 266: 16409–16414).

Tetanus toxin, when administered systemically or intramuscularly to animals, is selectively taken up by motor neurons in the brainstem and spinal cord (Habermann et al. (1973) *Naunyn-Schmiedebergs Arch. Pharmacol.* 276: 327–340). The clostridial neurotoxins, tetanus toxin and botulinum toxin, have a common binary structure in which the heavy chain appears to mediate binding, and the light chain is responsible for most of the toxicity. The carboxyl 451 amino acid fragment of the heavy chain ("tetanus toxin fragment C" or "TTC") retains the neuronal binding and uptake properties of the holotoxin without the toxic domains (Bizzini et al. (1977) *J. Neurochem.* 28: 529–542; Morris, et al. (1980) *J. Biol. Chem.* 255: 6071–6076; Weller et al. (1986) *Toxicon* 24: 1055–1063). TTC has been chemically conjugated to large proteins to enhance their uptake into neurons in tissue culture (Dobrenis et al. (1992) *Proc. Natl. Acad. Sci., USA* 89: 2297–2301) and neurons in animal models (Bizzini et al. (1980) *Brain Res.* 193: 221–227; Beaude et al. (1980) *Biochem. J.* 271: 87–91; Fishman et al. (1990) *J. Neurol. Sci.* 98: 311–325).

SUMMARY OF THE INVENTION

We have discovered that a hybrid protein comprising a human SOD-1 polypeptide with its carboxyl terminus fused to the amino terminus of TTC (with 13 intervening amino acid residues) is recognized by both anti-SOD and anti-TTC antibodies, is selectively taken up by neurons in a dose-dependent manner, and retains superoxide dismutase enzymatic activity after neuronal uptake. We have further discovered that the SOD-1/TTC hybrid protein undergoes retrograde axonal transport in neurons in an in vivo animal model system.

Based on these discoveries, the invention features a hybrid protein comprising an enzymatically active Cu/Zn superoxide dismutase moiety and a tetanus toxin fragment C moiety, wherein the tetanus toxin fragment moiety selectively delivers the hybrid protein into neurons, and the Cu/Zn superoxide dismutase moiety retains substantial enzymatic activity following neuronal uptake.

The invention also features an isolated recombinant DNA molecule encoding a hybrid protein comprising an enzymatically active Cu/Zn superoxide dismutase moiety and a tetanus toxin fragment C moiety, wherein the tetanus toxin fragment moiety selectively delivers the hybrid protein into neurons, and the Cu/Zn superoxide dismutase moiety retains substantial enzymatic activity following neuronal uptake. The invention also features a host cell transformed with the recombinant DNA molecule. The transformed host cell is used to produce the SOD-1/TTC hybrid protein.

The invention also features a method of treating a mammal identified as having a neuronal disease or disorder associated with oxidative stress in neurons, said method comprising administering an effective amount of a hybrid protein comprising:

(a) an enzymatically active Cu/Zn superoxide dismutase (SOD-1) moiety that retains enzymatic activity following uptake of the hybrid protein into a neuron; and (b) a tetanus toxin fragment C (TTC) moiety capable of selectively delivering the hybrid protein into neurons.

As used herein, "intraneuronal deficiency of superoxide dismutase" means a cellular state wherein a neuron contains an insufficient amount of superoxide dismutase to protect the neuron against oxidative damage. This cellular state can result from a decrease in the amount of superoxide dismutase in the neuron, or an increase in the amount of oxidative stress in the neuron, or both.

As used herein, "oxidative stress" means the cytotoxic consequences of oxygen radicals, i.e., superoxide anion ($\bullet O_2^-$), hydroxyl radical ($\bullet OH$), and hydrogen peroxide ($H_2O_2$), which are generated as byproducts of normal and aberrant metabolic processes that use molecular oxygen ($O_2$).

As used herein, "TTC" means tetanus holotoxin amino residues 865–1315. It should be noted that sometimes, in the art, "TTC" is used, in a broad sense, to refer to polypeptides that include tetanus holotoxin residues 865–1315 plus a carboxyl terminal portion of the tetanus toxin fragment B (at the amino end of TTC). Herein, to avoid ambiguity, such a TTC-containing sequence that contains additional amino acid residues at the amino end of TTC will be referred to as a "TTC moiety," or a the presence of additional amino acid residues will be noted.

Other features and advantages of the invention will be apparent from the following description of the preferred embodiments thereof, and from the claims.

DETAILED DESCRIPTION

Figure 1:
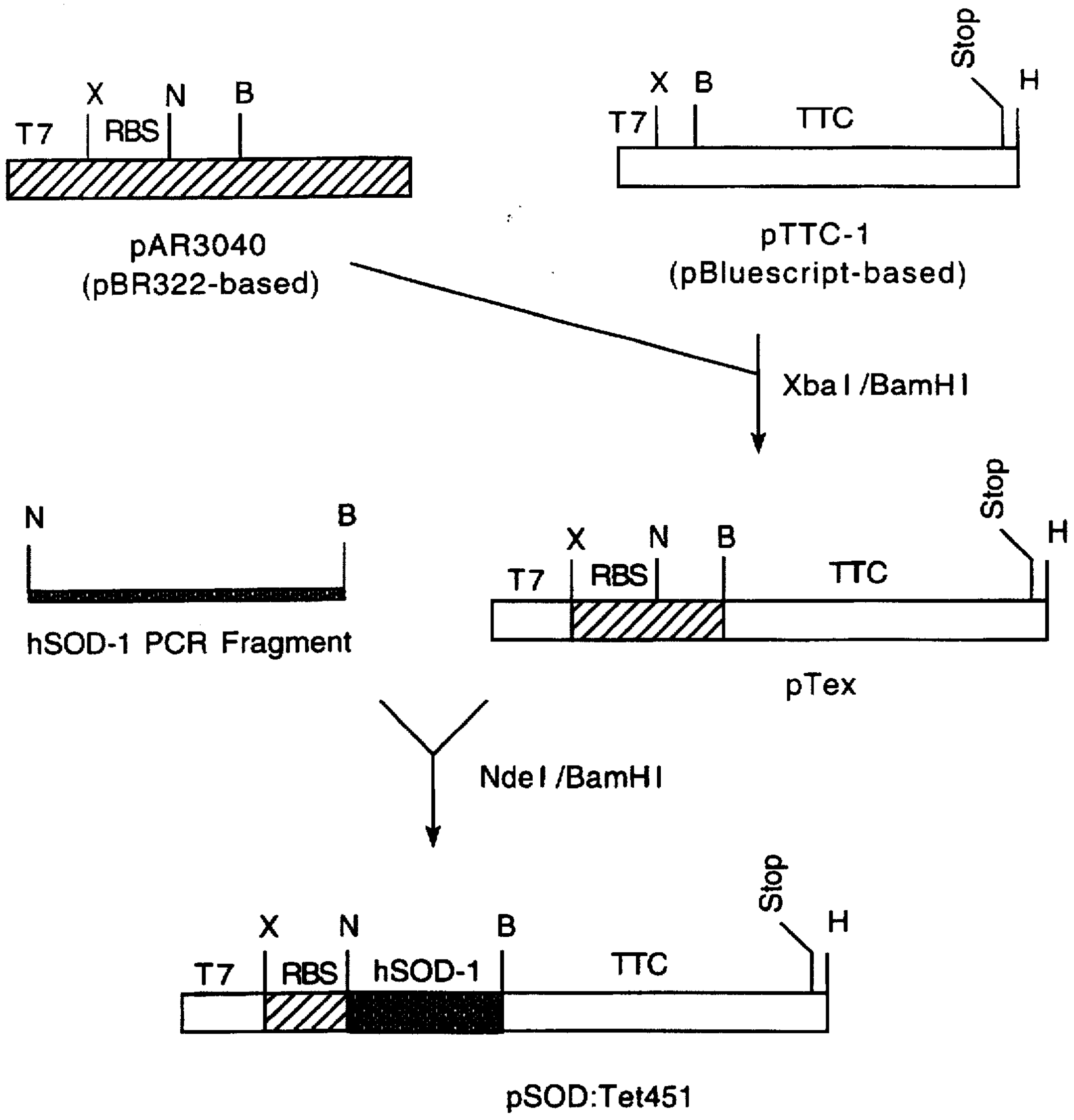
FIG. 1 is a schematic diagram illustrating the construction of plasmid pSOD:Tet451.

The present invention provides a SOD-1/TTC hybrid protein and DNA encoding the hybrid protein. The SOD-1/TTC hybrid protein combines the following properties: (1) it exhibits Cu/Zn SOD enzymatic activity; (2) it selectively binds to, and is taken up by, nerve cells, i.e., neurons; and (3) it retains substantial SOD enzymatic activity following cellular uptake.

By virtue of this combination of properties, the SOD-1/TTC hybrid protein of this invention can be used therapeutically to treat a mammal that has been identified as having a neuronal disease or disorder associated with oxidative stress in neurons, particularly oxidative stress resulting from an intraneuronal deficiency of SOD activity. The basis of the treatment with the hybrid protein is that the TTC moiety causes selective uptake of the hybrid protein by neurons and retrograde axonal transport within the neurons. Following the TTC-dependent neuronal uptake of the hybrid protein, the SOD activity of the SOD-1 moiety ameliorates oxidative stress in the neuron by removing ("scavenging") superoxide radicals.

While it is understood that the oxidative stress treated with the SOD-1/TTC hybrid protein of this invention will often be related to an intraneuronal deficiency of SOD activity, oxidative stress in neurons resulting from other causes can also be treated with the SOD-1/TTC hybrid protein. Examples of neurological diseases or disorders believed to be related to an intraneuronal deficiency of SOD activity include stroke, brain hypoxia-reperfusion, trauma, epilepsy, and age related degenerative disorders of the brain, such as Parkinson's disease, Huntington's disease, and amyotrophic lateral sclerosis. Individuals with such neurological diseases or disorders can be identified by medical practitioners trained in the relevant areas of medical practice. The compositions and methods of this invention can be used to treat any mammal, including humans.

The SOD-1/TTC hybrid protein can be used to ameliorate oxidative stress in neurons of the peripheral nervous system or central nervous system ("CNS"). By virtue of TTC-mediated uptake by neurons, retrograde axonal transport within neurons, and retrograde transsynaptic transfer between neurons, the SOD-1/TTC hybrid protein can be delivered from the peripheral nervous system into the CNS. Consequently, the SOD-1/TTC hybrid protein can be delivered across an intact blood-brain barrier.

In the practice of this invention, the SOD-1/TTC hybrid protein is administered by a parenteral route, e.g., intrathecal, intracerebral ventricular, intravenous, intramuscular or subcutaneous. Preferably, the route of administration is directly into the CNS, e.g., intrathecal or intracerebral ventricular, particularly if the mammal undergoing treatment is a human patient. Most preferably, the route of administration is intrathecal.

Administration of the SOD-1/TTC hybrid protein directly into the CNS is advantageous, because the CNS is generally shielded from the mammalian body's immune system. Avoiding exposure of the SOD-1/TTC hybrid to the immune system is preferred, because human patients are likely to have been previously immunized against tetanus. Tetanus vaccines typically contain inactivated tetanus holotoxin. Antibodies against the inactivated tetanus holotoxin could potentially recognize the TTC moiety of the SOD-1/TTC hybrid protein, and thereby interfere with its in vivo effectiveness.

The SOD-1/TTC hybrid protein can be formulated in any pharmaceutically acceptable dosage form. Preferably, the dosage form is suitable for parenteral administration. The dosage forms can include pharmaceutically acceptable excipients, carriers, buffers, osmotic agents, and the like, which are known in the art. See, e.g., *Remington's Pharmaceutical Sciences* (E. W. Martin). Preferably, pharmaceutical compositions according to this invention provide SOD-1/TTC hybrid protein in an aqueous physiological buffer solution containing the hybrid protein at a concentration in the range of 1 to 100 mg/ml. More preferably the concentration is in the range of 10 to 30 mg/ml.

The SOD-1/TTC hybrid protein can be used as the sole active ingredient in a pharmaceutical composition. Alternatively, the composition can be formulated to include active ingredients that augment or potentiate the therapeutic activity of the SOD-1/TTC hybrid protein. The selection of other active ingredients will depend on considerations such as the particular neurological disease(s) or disorder(s) for which the composition is to be used, and potential adverse drug interactions.

In the practice of this invention, SOD-1/TTC hybrid protein dose levels and time intervals will depend on variables such as the neurological disease or disorder being treated, the extent or severity of the disease or disorder, and the age, size, and overall physical condition of the mammal undergoing treatment. Preferably, the dose level is within the range of 10 μg/kg body weight/day to 100 mg/kg body weight/day. More preferably, the dose level is within the range of 100 μg/kg body weight/day to 10 mg/kg body weight/day.

The preferred method for obtaining the SOD-1/TTC hybrid protein of this invention is recombinant production, which involves genetic transformation of a host cell with a recombinant DNA vector encoding the SOD-1/TTC hybrid protein, expression of the recombinant DNA in the transformed host cell, and collection and purification of the hybrid protein. Preferably, the host organism is unicellular. More preferably, the host organism is prokaryotic.

The nucleotide sequence encoding the SOD-1/TTC hybrid protein must be operatively linked to suitable expression control sequences, and is typically incorporated into an expression vector, using conventional recombinant DNA techniques. See generally, Sambrook et al, *Molecular Cloning—A Laboratory Manual*, Cold Spring Harbor Press (1989); Ausubel et al. (eds.) *Current Protocols in Molecular Biology*, John Wiley & Sons, Inc. (1994). The design and construction of suitable expression vectors for producing the SOD-1/TTC hybrid protein is within ordinary skill in the art.

The expression vector is selected to be compatible with the host organism. A wide variety of host/expression vector combinations can be employed for expressing the SOD-1/TTC-encoding DNA. Numerous host cell lines, expression vectors, and expression vector components are commercially available. Compatible host/expression vector combinations can be readily selected by those of skill in the art. In a preferred embodiment of the invention, the unicellular host organism is *E. coli*, and the expression vector is pBluescript K+(Stratagene, LaJolla, Calif.).

The complete amino acid sequence of tetanus holotoxin and the *C. tetani* DNA sequence that encodes it have been published (Eisel et al. (1986) *EMBO J.* 5: 2495–2502; Fairweather et al. (1986) *Nuc. Acids. Res.* 14: 7809–7812). In addition, the TTC portion of the sequence has been defined, and TTC has been cloned and expressed (Fairweather et al. (1986) *J. Bacteriol.* 165: 21–27; Halpern et al. (1990) *Infection and Immunity* 58: 1004–1009). Accordingly, a DNA clone encoding the TTC moiety of the hybrid protein of this invention can be obtained by one of ordinary skill in the art, using a publicly available strain of *C. tetani* (e.g., from the American Type Culture Collection), published sequence information (e.g., Eisel et al., supra; Halpern et al., supra) and conventional recombinant DNA techniques. Preferably, the TTC DNA clone used to produce a DNA construct encoding SOD-1/TTC is obtained by convention polymerase chain reaction ("PCR") techniques, as described by Halpern et al. (supra). General references on PCR techniques include *PCR Technology*, Erlich (ed.), Stockton Press, New York, 1989; and *PCR Protocols*, Innis et al. (eds.), Academic Press, San Diego, 1990).

The complete amino acid sequence of human SOD-1 and the DNA sequence that encodes it have been published (Sherman et al. 1983) *Proc. Natl. Acad. Sci. USA* 80: 5465–5469). Preferably, the SOD-1 DNA clone used to produce a DNA construct encoding SOD-1/TTC is obtained by conventional PCR techniques. An actual example of a specific procedure for isolating a human SOD-1 clone by PCR techniques is provided below, under the "Plasmid Construction."

The human population may exhibit some polymorphism at the SOD-1 genetic locus. See, e.g., Sherman et al. (supra). As a result of polymorphism, minor variations in the amino acid sequence of the SOD-1 moiety of the hybrid protein of this invention may occur, depending on the source of the human SOD-1 clone used to construct the SOD-1/TTC DNA coding region. For purposes of this invention, such SOD-1 polymorphism is of no consequence, as long as adequate SOD enzymatic activity remains. SOD-1/TTC hybrid proteins containing minor amino acid sequence variations as a result of natural SOD-1 polymorphism are within the scope of this invention.

The design of the SOD-1/TTC hybrid protein can vary without departing from the scope of the invention, as long as the hybrid protein comprises an enzymatically active SOD amino terminal moiety and a functional TTC carboxyl terminal moiety. Preferably the hybrid protein comprises the entire SOD-1 amino acid sequence and the entire TTC sequence (amino acid residues 865–1315 of the tetanus holotoxin). Additional amino acid residues may be present at the ends of the hybrid protein moieties without disrupting hybrid protein function. Such optional additional amino residues may be artifacts of the plasmid construction process, and may be left in place as a matter of convenience. For example, in a preferred embodiment of the invention, a SOD-1/TTC hybrid protein, designated SOD:Tet451 (SEQ ID NO:5), has the following structure (amino terminus to carboxyl terminus): full-length human SOD-1, followed by four amino acids encoded by restriction enzyme cloning sites, followed by amino acids 856–1315 of tetanus holotoxin (i.e., the carboxyl terminal 451 amino acid residues, which constitute TTC, plus the nine heavy chain amino acid residues immediately preceding the amino terminus of TTC).

Although the amino acid sequence of SOD:Tet451 is disclosed herein (SEQ ID NO:5) as comprising an amino-terminal methionine, it is possible that the amino-terminal methionine is removed following production of SOD:Tet451 in *E. coli*. Experimental data on the removal of the amino-terminal methionine residue of SOD:Tet451 in *E. coli* have not been obtained. Preferably, the amino-terminal methionine residue of the SOD-1/TTC hybrid is removed. Such removal is optional, however, as long as the biological activities of both the SOD-1 moiety and the TTC moiety are retained. In general, the removal of amino-terminal residues varies, depending on the protein involved and type of cell in which the protein is expressed.

The SOD-1/TTC hybrid protein binds to both anti-human SOD-1 antibodies and anti-TTC antibodies. Accordingly, either type of antibody can be used in analytical procedures, e.g., immunoblotting. Either type of antibody can also be used to prepare immunoaffinity columns for affinity chromatography of SOD-1/TTC hybrid proteins.

Preferred recombinant SOD-1/TTC purification schemes comprise the steps of ammonium sulfate precipitation and immunoaffinity chromatography, with ammonium sulfate precipitation preceding immunoaffinity chromatography. Purities of approximately 50–80% can be achieved in a purification scheme using only those two steps. Additional purification steps, using conventional techniques, can be added by those of ordinary skill in the art, in order to obtain SOD-1/TTC sufficiently pure to be acceptable for use in pharmaceutical compositions. Examples of preferred additional purification steps include size exclusion HPLC (preferably after the immunoaffinity chromatography step), gel filtration chromatography (preferably after the ammonium sulfate precipitation step and before the immunoaffinity chromatography step), and ion exchange chromatography (preferably after the ammonium sulfate precipitation step and before the immunoaffinity chromatography step).

EXPERIMENTAL INFORMATION

Plasmid Construction

The TTC cDNA from plasmid SS1261 (obtained from Dr. J. Halpern) (Halpern et al. (1990) *Infecti. Immun* 58: 1004–1009), encoding amino acids 856–1315 of tetanus holotoxin, was cloned into pBluescript KS+(Stratagene, La Jolla, Calif.) as a BamH I/HinD III fragment, to yield plasmid pTTC-1. The ribosome binding site and translation initiation signals (Xba I/BamH I fragment) from pAR3040 (Novagen, Madison, Wis.) were transferred to pBluescript (which contains a T7 promoter), to yield vector pBex. They were also transferred into pTTC-1, to yield plasmid pTex (FIG. 1). High-copy number vectors such as pBluescript are not customarily used for protein expression in bacteria, in part because the encoded proteins may be expressed constitutively. While our encoded proteins were expressed to varying extents prior to induction, this expression did not appear to interfere with bacterial growth or the stability of the product.

A cDNA clone for wild-type human SOD-1 was isolated from a lymphoblastoid cell line using reverse transcriptase-polymerase chain reaction ("RT-PCR") techniques, and cloned into pBluescript KS+. The RT-PCR primers, which incorporated EcoR I restriction sites for cloning, were as follows (upstream and downstream, respectively):

5'GGAATTCGTT TGCGTCGTAG TCTCCTGCA 3' (SEQ ID NO:1);

5'GGAATTCTTC TGACAAGTTT AATACCCAT 3' (SEQ ID NO:2).

Subsequently, PCR was used to prepare two modified SOD-1 cDNAs for subcloning. Both reactions used an upstream primer consisting of:

5' GGGAATTCCA TATGGCGACG AAGG 3' (SEQ ID NO:3), to convert the ATG translation start codon for SOD-1 into an Nde I restriction site. One PCR reaction used a downstream primer homologous to the T3 promoter in Bluescript. This modified cDNA was cloned into pBex as an Nde I/HinD III fragment, for bacterial expression of wild-type recombinant human SOD-1 (pBex:SOD-1, for production of rhSOD-1). In a separate PCR reaction, the downstream primer, 5' CGCGGATCCTTGGGCGATCCCAAT 3' (SEQ ID NO:4) substituted a BamH I restriction site for the SOD-1 translation stop. The product Nde I/BamH I fragment was cloned into the corresponding sites in pTex to obtain plasmid pSOD:Tet451 (FIG. 1).

Plasmid pSOD:Tet451 encoded the desired hybrid protein, SOD:Tet451, which consisted of full-length human SOD-1 followed by 4 amino acids encoded by restriction enzyme cloning sites (BamH I and Sal I), followed by amino acids 856–1315 of tetanus holotoxin (i.e., the carboxyl terminal 451 amino acids of tetanus toxin heavy chain, which constitute TTC, plus the nine heavy chain amino acids immediately preceding the amino terminus of TTC). In plasmid pSOD:Tet451, the complete SOD-1/TTC coding region consisted of (SEQ ID NO:6).

Plasmids pBex:SOD-1 and pSOD:Tet451 were used to transfect *E. coli* strain BL21DE3, which carried the phage gene for T7 polymerase (Novagen, Madison, Wis.), for protein expression. Overnight cultures were diluted 1:50 in NZCYM media plus 0.1 mM $CUSO_4$, 0.1 mM $ZnCl_2$, and 100 μg/ml ampicillin, and grown for several hours at 37° C. Isopropylthio-β-D-galactoside (1 mM) was then added to induce the expression of T7 polymerase and, indirectly, the desired recombinant proteins.

Purification of Recombinant Proteins

Bacteria from induced cultures were pelleted by centrifugation for 10 minutes at 4000×g. The pellets were resuspended in 50 mM potassium phosphate buffer (pH 7.8) containing 0.1 mM EDTA, 0.1% Triton X-100, 0.1% β-mercaptoethanol, 0.2 mM phenylmethylsulfonyl fluoride, 1 μg/ml leupeptin, 1 μg/ml pepstatin, and 0.2 mg/ml lysozyme. Following sonication, total bacterial lysates were centrifuged at 30,000×g for 20 minutes at 4° C. The resulting supernatants (soluble fractions) and pellets (insoluble fractions) were stored frozen at −20° C. until further use. Protein concentrations were determined using a commercial Coomassie Blue reagents (Pierce, Rockford, Ill.) (for lysates) or a bicinchoninic acid protein assay (for immunoaffinity-purified samples) (Pierce, Rockford, Ill.).

Recombinant protein expression and purification were initially evaluated by SDS-PAGE (Laemmli (1970) *Nature* 227: 680–685). For immunoblotting, proteins were separated on 4–15% gradient mini-gels (Bio-Rad, Melville, N.Y.), and electrophoretically transferred onto nitrocellulose (0.2 μm porosity, Bio-Rad, Melville, N.Y.) (Towbin (1979) *Proc. Natl. Acad. Sci. USA* 76: 4350–4354). Antibody detection of blotted proteins was done with a Vectastain ABC-alkaline phosphatase kit (Vector Laboratories, Burlingame, Calif.). Primary antibody against human SOD-1 (sheep anti-SOD-1 total IgG fraction from The Binding Site, San Diego, Calif.) was used at a concentration of 1.5 μg/ml. Primary antibody against TTC (rabbit anti-TTC whole antisera, Calbiochem, La Jolla, Calif.) was used at a dilution of 1:20,000.

SOD:Tet451 was precipitated from the bacterial lysis supernatant by addition of ammonium sulfate to 45% saturation. Wild-type recombinant human SOD-1 was obtained from the soluble lysate fraction as a 60–90% ammonium sulfate fraction. The precipitates were resolubilized in 50 mM potassium phosphate buffer (pH 7.8) containing 0.1 mM EDTA, 0.2 mM phenylmethylsulfonyl fluoride, 1 μg/ml leupeptin, and 1 μg/ml pepstatin, and dialyzed to remove the ammonium sulfate. Immunoaffinity columns were prepared by immobilizing sheep anti-human-SOD-1 total IgG, or rabbit anti-TTC total IgG, to a hydrazide support, according to vendor's instructions (Pierce, Rockford, Ill.). For a typical affinity chromatography run, 8–10 mg (1 ml) of solubilized protein from the indicated ammonium sulfate fraction was adjusted to 150 mM NaCl and incubated on the column overnight at 4° C. The column was then washed extensively with PBS containing antiproteases prior to elution of bound material with 50 mM sodium bicarbonate (pH 11.0). The eluted column fractions were immediately neutralized with 3 M sodium acetate (pH 5.2). Column fractions containing significant amounts of protein as assessed by their optical density at 280 nm were pooled and concentrated using a Centricon-50 (for SOD:Tet451) or Centricon-10 (for recombinant SOD-1) (Amicon, Beverley, Mass.).

SOD-1 Enzyme Activity Assays

Superoxide dismutase activity of recombinant proteins and commercial human SOD-1 prepared from erythrocytes (Sigma, St. Louis, Mo.) was determined using slight modifications of previously described methods (Beauchamp et al. (1971) *Anal. Biochemi.* 44: 276–287; Beyer et al. (1987) *Anal. Biochem.* 161: 559–566; McCord et al. (1969) *J. Biol. Chem.* 259: 12756–12762). This colorimetric assay is based on the ability of SOD to inhibit the superoxide-mediated reduction of nitroblue tetrazolium to formazan. For each protein tested, a concentration-response curve was constructed using a linear transformation of SOD-1 dose-response data as previously published (Asada et al. (1974) *Agric. Biol. Chem.* 38: 471–473). Transformed data were subjected to least squares linear regression, and specific activities (units SOD/mg protein) of the various proteins were then determined by deriving the mass of sample protein which produced 50% inhibition of the SOD-inhibitable nitroblue tetrazolium reduction.

Immunocytochemistry

N18-RE-105 cells were plated on 4-well Lab-Tek™ chambered slides (Nunc, Napierville, Ill.) pretreated overnight with 20 μg/ml poly-L-lysine) at $1\times10^4$ cells/0.5 ml/well and cultured as described previously with minor modifications (Malouf et al. (1984) *J. Biol. Chem.* 259: 12756–12762). Cells were cultured for 3 days prior to use in indirect immunofluorescence experiments, when the cells were fixed in 2% formalin/PBS for 10 minutes at room temperature. After extensive washing, commercial recombinant TTC (Boehringer-Mannheim, Indianapolis, Ind.) or experimental protein preparations were diluted in PBS/0.1% bovine serum albumin and added at room temperature for 2 hours. The cells were then incubated for 1 hour in primary antibody, i.e., rabbit anti-TTC antisera at 1:1000 dilution (Calbiochem, La Jolla, Calif.), followed by a 1 hour incubation with fluorescein-conjugated goat anti-rabbit IgG, at 1:100 dilution (Boehringer-Mannheim, Indianapolis, Ind.). Cells were mounted in PBS:glycerol (1:1) containing 1 mg/ml propyl-gallate as an antifading agent and photographed at an objective magnification of 40X, using a Zeiss™ axiophot epifluorescent microscope with a fluorescein filter set.

E18 rat hippocampal cells were cultured in serum-containing media using previously described methods (Banker et al. (1977) *Brain Res.* 126: 397–425; Walicke et al. (1986) *Proc. Natl. Acad. Sci., USA* 83: 3012–3016). Bilateral hippocampi were dissected in $Ca^{2+}/Mg^{2+}$-free Hanks Balanced Salt Solution (Gibco) and dissociated by brief trypsin digestion and trituration. The final cell suspension was plated $7\times10^4$/0.2 ml/well on 4-well Lab-Tek™ chambered slides (Nunc), which were pretreated for 3 hours with 10 μg/ml poly-L-lysine in 100 mM borate buffer (pH 8.4). Cells were maintained at 37° C., under humidified conditions of 5% carbon dioxide/95% air. The cultures were used for immunocytochemical experiments after 6 days in vitro. These studies were carried out as described above for the N18-RE-105 cells with the following additions: (i) the incubation of the cells with primary antibody following exposure to SOD:Tet451 included both rabbit anti-TTC antisera and mouse monoclonal antibody against glial fibrillary acidic protein (Sigma, 1:500 final dilution), and (ii) accordingly, the second antibody incubation included both fluorescein-conjugated goat anti-rabbit IgG as well as rhodamine-conjugated goat anti-mouse IgG (Sigma, 1:100 final dilution).

Binding/Internalization of SOD:Tet451 in Cultured Neuronal Cells

N18-RE-105 cells were plated onto Costar™ 12-well culture clusters (Costar, Cambridge, Mass.) at $1\times10^5$ cells/ml/well and were used for experiments after 3 days in vitro. Alternatively, hippocampal cells were plated at $3.5\times10^5$ cells/0.5 ml/well and were used after 8–10 days in vitro. These primary cultures were treated with 5 μM 5-fluoro-2'-deoxyuridine (Sigma) after 3 days in vitro to inhibit the proliferation of non-neuronal cells. Hippocampal cultures grown under these conditions typically resulted in a cell population which was 90% neurofilament-positive after two weeks in vitro (Francis et al. (1991) Soc. for Neuroscience Abstract).

The effect of dose on the association of SOD:Tet451 with N18-RE-105 cells or hippocampal neurons was examined by incubating the cells with various concentrations of hybrid protein in DMEM for one hour at 37° C. The relative efficiency of SOD:Tet451 vs native human SOD-1 for raising levels of cell-associated human SOD-1 in hippocampal cultures was studied under the same incubation conditions using a fixed concentration of ligand.

Hybrid protein internalization was assessed using a protocol modified from previous studies of tetanus toxin internalization into N18-RE-105 cells (Staub et al. (1986) *J. Neurosci.* 6: 1443–1451) or PC12 cells (Sandberg et al. (1989) *J. Biol. Chem.* 264: 5679–5686). Like these earlier studies, our experiments used a specialized binding buffer (0.25% sucrose, 20 mM Tris-acetate, 30 mM NaCl, 1 mM $CaCl_2$, 1 mM $MgCl_2$, 0.25% bovine serum albumin (pH 7.0)) for incubation of the cells with SOD:Tet451, in order to optimize levels of cell-associated hybrid protein. N18-RE-105 cells were incubated with 2 μg/ml SOD:Tet451 for one hour, at 0° C. or 37° C. After this, half of the cells at each temperature were incubated with 0.1 μg/ml pronase E (Sigma) for 10 minutes at 37° C., followed by washing with a cocktail of anti-proteases (5 mM amino caproic acid, 1 mM benzamidine, 1 mM phenylmethylsulfonyl fluoride). This pronase digestion paradigm was also used to look at the cellular persistence of hybrid protein after pulse treatment of cells with SOD:Tet451. Cells were incubated in DMEM with 2 μg/ml of SOD:Tet451 for one hour at 37° C. Following removal of the hybrid protein, the cells were washed and incubated at 37° C. in DMEM for various amounts of time prior to the pronase step. For all experiments dealing with the interaction of SOD:Tet451 with living N18-RE-105 cells or hippocampal cultures, cells were pelleted, and lysed using previously described methods (Miyamoto et al. (1989) *J. Pharmacol. Exp. Ther.* 250: 1132–1140; Murphy et al. (1989) *Neuron* 2: 1547–1558). Lysates were clarified by centrifugation for 5 minutes at 1000×g.

EIA for human SOD-1

Hybrid protein binding and internalization into intact neuronal cells was analyzed through the use of a two antibody sandwich EIA specific for human SOD-1. Corning™ 96-well polystyrene ELISA plates (Fisher Scientific, Pittsburgh, Penna.) were coated with 10 μg/0.1 ml/well of sheep anti-human SOD-1 total IgG (The Binding Site, San Diego, Calif.) in 100 mM sodium carbonate buffer, pH 9.6. The plates were incubated for 4 hours at 37° C. and then stored overnight at 4° C. The next day, the wells were washed and blocked for 15 minutes with 1% bovine serum albumin in wash buffer (PBS (pH 7.4) containing 0.02% thimerosal and 0.05% Tween-20). The blocking solution was aspirated and 50 μl of mouse anti-human SOD-1 (Sigma, 1:5000 final dilution) was added along with either 50 μl of SOD:Tet451 (standard curve) or 50 μl of cell lysate. The antibody/antigen mixture was incubated at room temperature for 3 hours, the wells were washed, and bound mouse antibody was detected with 0.1 ml/well of alkaline phosphatase-conjugated goat anti-mouse IgG (Boehringer Mannheim, Indianapolis, Ind.; 1:2000 final dilution). The plate was incubated at room temperature for 1 hour, and the wells were washed 4 times prior to the addition of alkaline phosphatase substrate. The enzyme reaction was initiated by adding 0.2 ml/well of 4-nitrophenyl phosphate (Boehringer Mannheim, 1 mg/ml in 10 mM diethanolamine (pH 9.5)). The rate of change in absorbance at 405 nm was measured at ambient temperature with a Thermomax™ microplate reader (Molecular Devices, Menlo Park, Calif.) in conjunction with Softmax for Windows software (Molecular Devices, Menlo Park, Calif.). The concentration of SOD:Tet451 in N18-RE-105 cell lysates was derived from a hybrid protein standard curve with a linear concentration range of 1.6–25 ng/ml.

SDS-PAGE and Western Blot Analysis

Soluble protein fractions from bacterial lysates containing the SOD:Tet451 hybrid protein or recombinant human SOD-1 were subjected to SDS-PAGE analysis performed under reducing conditions. Compared to the soluble protein fraction obtained from bacteria containing the expression plasmid without an insert, SOD:Tet451 extracts showed a novel, minor band at the predicted subunit molecular mass of 68 kd. The soluble extract from bacteria expressing wild-type human SOD-1 also revealed a novel band at the subunit molecular mass of approximately 19 kd. The identities of these bands were confirmed by Western blots using antibodies against human SOD-1 and TTC. As evidenced by the presence of a single major immunoreactive band in each recombinant protein extract, the proteins were obtained from the soluble lysate fraction predominantly as full-length products. Although recombinant human SOD-1 represents a substantial portion of the total bacterial protein in some preparations (estimated on Coomassie blue gels at 20–30%), SOD:Tet451 is uniformly expressed at a lower level. The lower expression level for the hybrid protein incorporating TTC is consistent with previous reports that the unmodified TTC coding sequence is not expressed well in *E. coli* (Eisel et al. (1986) *EMBO J* 5: 2495–2502; Fairweather et al. (1986) *J. Biol. Chem.* 165: 21–27; Makoff et al. (1989) *Nuc. Acids Res.* 17: 10191–10202). The bacterially-produced human SOD-1 protein showed a reduced mobility on SDS-PAGE gels relative to that predicted by its amino acid composition, as has been previously reported (Hallewell et al. (1985) *Nuc. Acids Res.* 13: 2017–2036; Hartman et al. (1986) *Proc. Natl. Acad. Sci., USA* 83: 7142–7146). The higher molecular weight band detected in the recombinant human SOD-1 sample by the anti-SOD-1 antibodies is likely to be incompletely reduced/denatured human SOD-1 dimers (Hartz et al. (1972) *J. Biol. Chem.* 247: 7043–7050).

Figure 2:
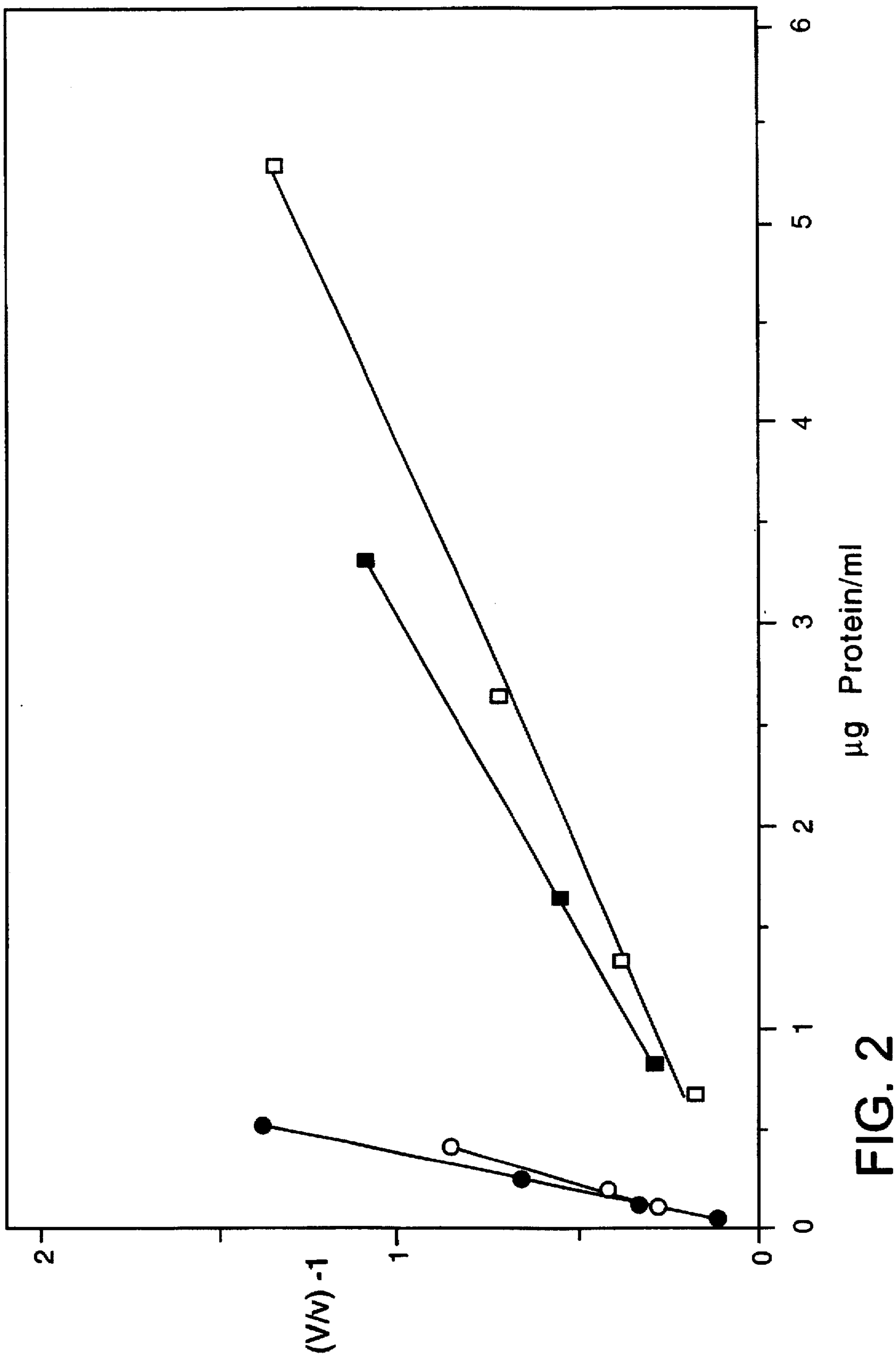
FIG. 2 is a graph of SOD activity as a function of protein (SOD enzyme preparation) concentration, for commercial human SOD (closed circles); affinity-purified recombinant human SOD-1 (open circles); SOD:Tet451 affinity purified using SOD antibodies (closed squares); and SOD:Tet451 affinity purified using TTC antibodies (open squares). Data are plotted according to Asada et al. (1974) *Agric. Biol. Chem.* 38: 471–473. Concentration-response curves were linear for all samples tested (r>0.995).

Immunoaffinity purified samples of SOD:Tet451 showed significant enrichment of the 68 kd protein as determined by SDS-PAGE analysis. This protein was recognized on immunoblots by antibodies against either SOD-1 or TTC, and affinity purified material appeared identical by SDS-PAGE and Western blotting regardless of whether anti-SOD-1 or anti-TTC antibodies were used in the purification (not shown). For wild-type human SOD-1, affinity-purified samples showed a subunit molecular mass of approximately 19,000 daltons following SDS-PAGE under reducing conditions (FIG. 2A). This protein was recognized on immunoblots by anti-SOD-1 but not anti-TTC antibodies.

Enzyme Activity

The enzymatic activities of commercial human SOD-1 isolated from erythrocytes, recombinant human SOD-1, and the SOD:Tet451 hybrid protein are summarized in Table 1. Table 1 shows data on SOD specific activity of commercial human SOD-1 and affinity-purified recombinant proteins. Specific activity was determined by estimating the sample protein concentration at which there was 50% inhibition of SOD-inhibitable nitroblue tetrazolium reduction ([V/v]−1=0.73 for this assay).

TABLE 1

| | SOD-1 Specific Activity | |
|---|---|---|
| Treatment | units/mg protein | units/nmole |
| Commercial SOD-1 | 3570 | 58 |
| Recombinant SOD-1 | 2940 | 47 |
| SOD:Tet451 anti-SOD | 460 | 33 |
| SOD:Tet451 anti-TTC | 360 | 26 |

The affinity-purified recombinant human SOD-1 possesses greater than 80% of the enzymatic activity present in the commercial preparation of human SOD-1. On a per milligram protein basis, SOD:Tet451 was only 10–13% as active as the commercial enzyme. However, due to the greatly increased molecular mass of the hybrid protein relative to wild-type SOD-1, specific activity calculated on a basis of total protein does not accurately reflect the amount of activity retained by each molecule. When the enzymatic activities of the various proteins were calculated on a molar basis, the specific activities of the recombinant enzyme and the hybrid protein were more comparable (47 units/nmole vs. 26–33 units/nmole, respectively). The hybrid protein showed similar specific activity regardless of whether it was affinity-purified using anti-SOD-1 or anti-TTC antibodies. This suggests that the SOD activity present in the hybrid protein preparations is not due to SOD domains which lacked a TTC moiety before immunoaffinity purification. This interpretation is consistent with the results from our immunoblot analysis with anti-SOD-1 antibodies, in that SOD-1 immunoreactivity was associated with full-length hybrid protein and not with any potential contaminating cleavage or degradation products. The activities of all samples were inhibited by 1 mM KCN, confirming that the observed activities are due to the human Cu/Z SOD rather than bacterial SOD, which is not inhibited by KCN (Hartman et al. (1986) *Proc. Natl. Acad. Sci., USA* 83: 7142–7146).

Immunocytochemistry

To determine whether the SOD:Tet451 hybrid protein possesses the characteristic nerve cell binding properties of TTC, we first compared the immunocytochemical labeling profile of SOD:Tet451 to commercial recombinant TTC in the neuroblastoma hybrid cell line, N18-RE-105. Unlike most neuroblastoma cell lines, N18-RE-105 cells have a surface ganglioside composition similar to normal brain tissue and thus bind high amounts of tetanus toxin (Staub et al. (1986) *J. Neurosci.* 6: 1443–1451). Both recombinant TTC and the SOD:Tet451 hybrid protein bound to fixed N18-RE-105 cells. At equal protein concentrations, the labeling intensities for commercial TTC and SOD:Tet451 appeared to be equivalent. However, a 10-fold lower concentration of TTC showed markedly reduced labeling (data not shown). This finding suggests that the avidity of binding of SOD:Tet451 is similar to that of TTC. Labeling of NIS-RE-105 cells was similar for SOD:Tet451 affinity-purified on either an anti-SOD-1 or anti-TTC column. Thus, SOD:Tet451 labeling of fixed membranes is also likely to be due to the full-length, hybrid protein rather than smaller degradation products. We verified the neuron-specific binding properties of SOD:Tet451 through similar studies on primary, mixed cultures of embryonic rat hippocampus. The hybrid protein appeared to interact exclusively with neuronal cell bodies and processes. As defined by their positive immunoreaction with antibodies against glial fibrillary acidic protein, astrocytes were uniformly unlabeled by anti-TTC antibodies following incubation with SOD:Tet451. These findings are consistent with previous immunocytochemistry studies which have shown the neuron-specific binding of tetanus toxin or TTC (Critchley et al. (1985) *J. Cell Biol.* 100: 1499–1507; Halpern et al. (1990) *Infecti. Immun.* 58: 1004–1009; Mirsky et al. (1978) *Brain Res.* 148: 251–259).

Binding/Internalization in Cultured Neuronal Cells

Figure 3:
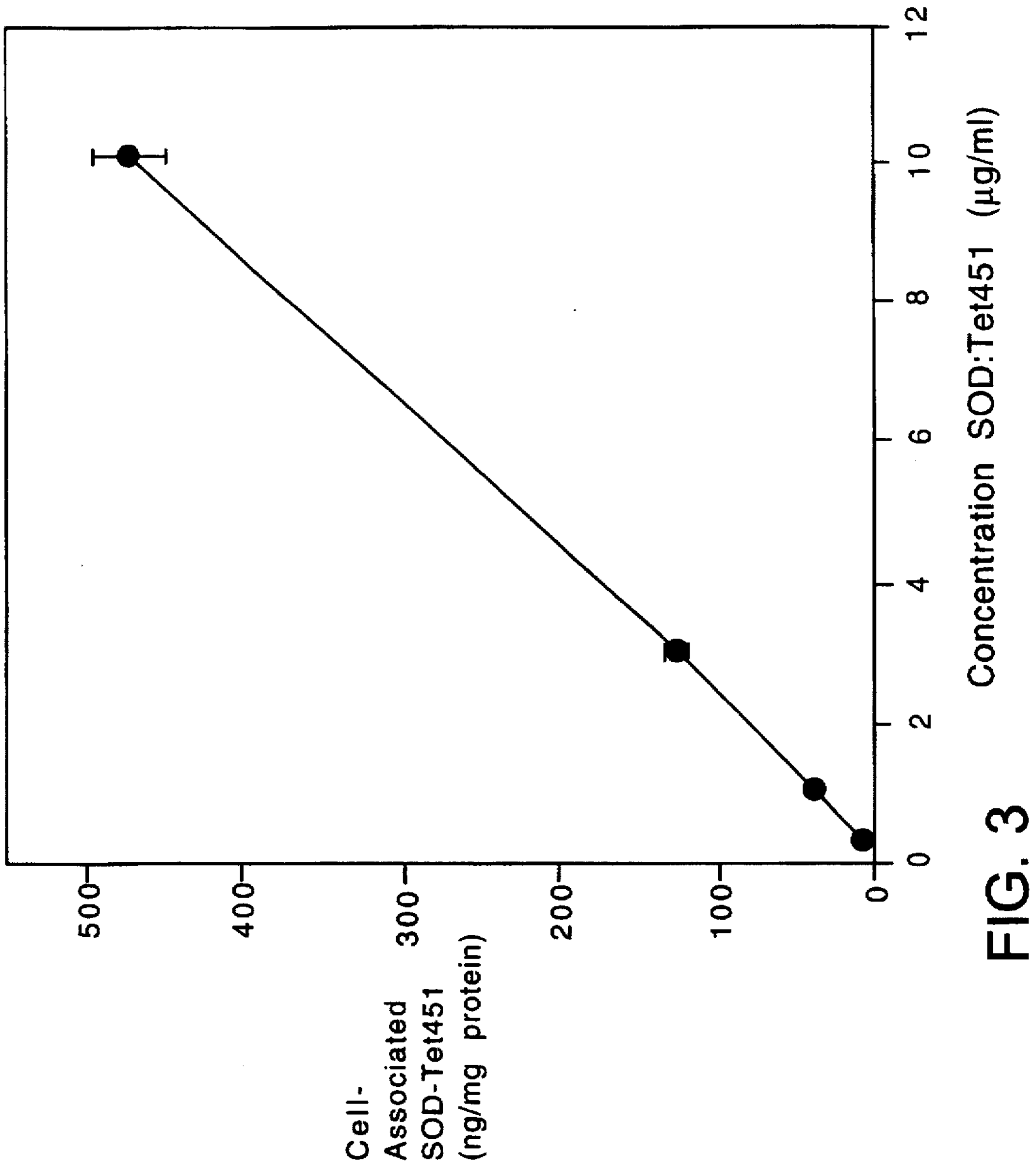
FIG. 3 is a dose-response curve for SOD:Tet451 association with N18-RE-105 cells. Cells were incubated at 37° C. for one hour with various concentrations of SOD:Tet451 in DMEM. Cell lysates were analyzed for cell-associated SOD:Tet451 by EIA specific for human SOD-1. Data points are means±S.E.M. of 4 or 5 replicates for each dose.

The capacity of SOD:Tet451 to deliver human SOD-1 to intact cultured neuronal cells was evaluated using an antibody-sandwich enzyme immunoassay (EIA) specific for human SOD-1. The N18-RE-105 cell line, like mammalian brain tissue, possesses high levels of endogenous SOD-1 (1–2 μg SOD-1/mg protein). Determination of cell-associated SOD:Tet451 by EIA allowed us to specifically assay for the hybrid protein human SOD-1 moiety in spite of a high background level of rodent SOD-1. Incubation of cells with increasing amounts of hybrid protein resulted in a dose-dependent increase in cell-associated SOD:Tet451 which was linear over the concentration range of 0.3–10 μg/ml (FIG. 3). N18-RE-105 cells incubated with 0.1 μg/ml SOD:Tet451 failed to show a level of cell-associated hybrid protein which could be reliably detected by our EIA, while limiting amounts of hybrid protein did not permit us to thoroughly examine treatment concentrations above 10 μg/ml.

Figure 4:
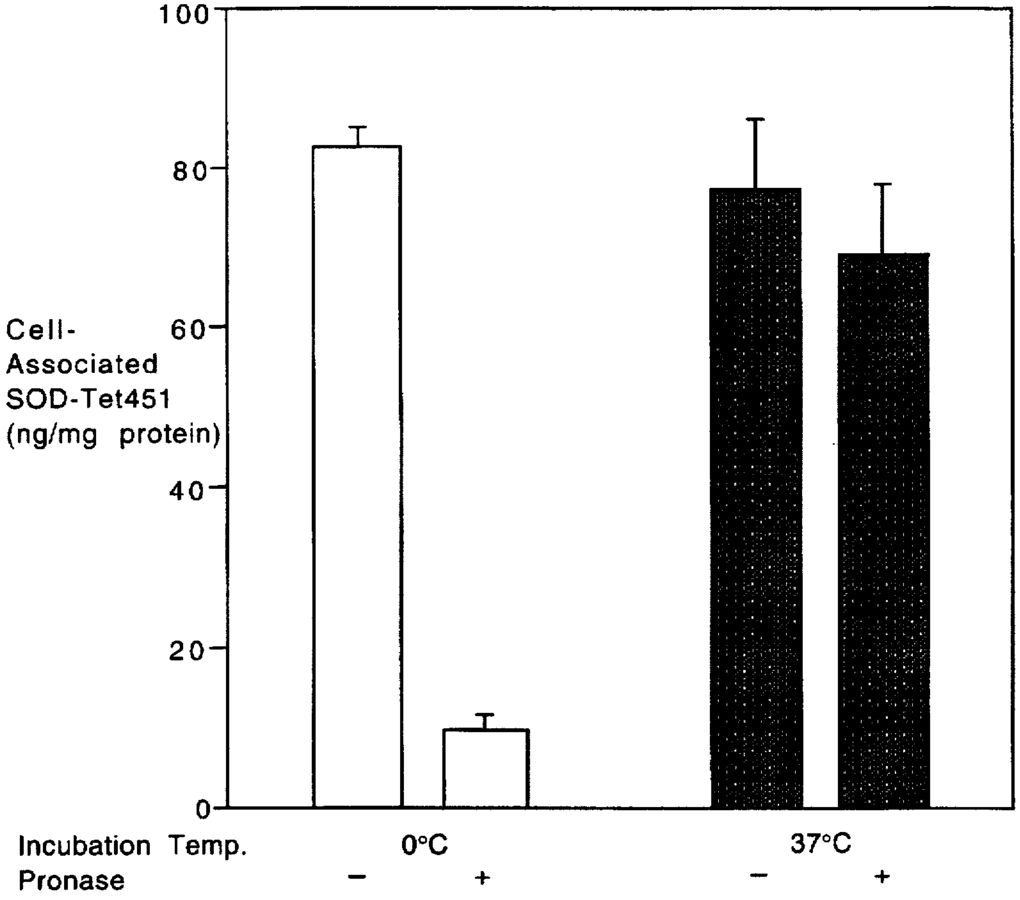
FIG. 4 is a bar graph summarizing data on the effect of pronase treatment on cell-associated SOD:Tet451 in N18-RE-105 cells. Cells were incubated for one hour, at 0° C. or 37° C., with a fixed concentration of SOD:Tet451 in binding buffer. Thereafter, half the cells at each temperature were briefly treated with pronase to define internalized SOD:Tet451. Cell lysates were analyzed for cell-associated SOD:Tet451, using an EIA specific for human SOD-1. Results are means±S.E.M. of 5 or 6 replicates for each treatment.
Figure 5:
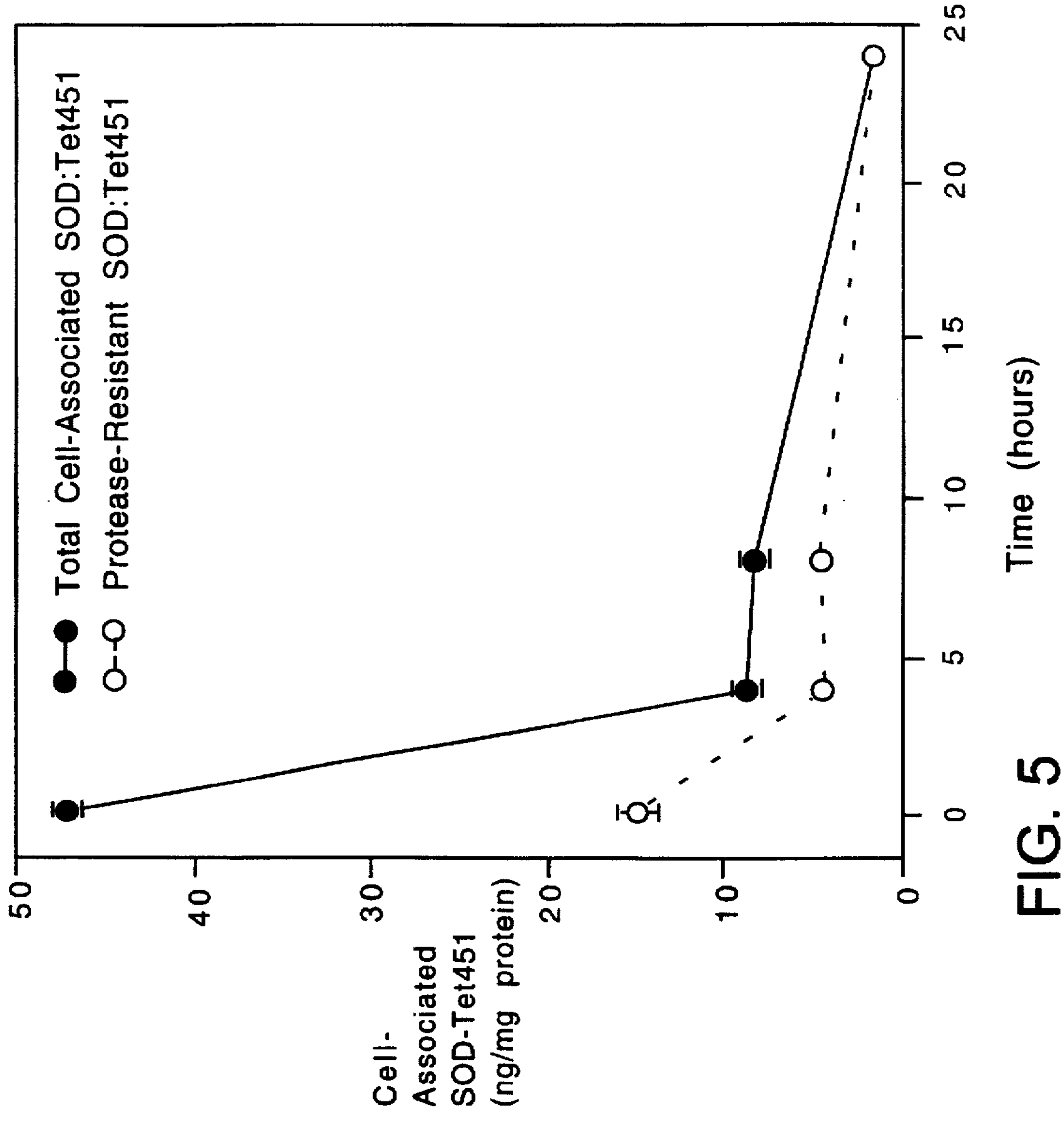
FIG. 5 is a graph illustrating the persistence of cell-associated SOD:Tet451 in N18-RE-105 cells following pulse incubation with SOD:Tet451. Cells were incubated at 37° C. for various amounts of time in DMEM containing a fixed concentration of SOD:Tet451. For each time point, half the cells were treated with pronase to define internalized SOD:Tet451. Results are means±S.E.M. of 4 or 5 replicates for each treatment.

To determine if the hybrid protein is internalized into N18-RE-105 cells, we examined whether cell-associated SOD:Tet451 is resistant to brief pronase treatment of intact cells. This experimental paradigm has been useful in previous studies of the internalization of tetanus toxin (Staub et al. (1986) *J. Neurosci.* 6: 1443–1451; Sandberg et al. (1989) *J. Biol. Chem.* 264: 5679–5686), and is based on the observation that binding into a cell-surface membrane (pronase sensitive) compartment is not a temperature-dependent process whereas internalization (movement of the ligand to a pronase resistant location) is reduced at low temperature. Similar to these earlier reports, our internalization study used a low ionic strength, neutral pH binding buffer to optimize cellular binding of SOD:Tet451 under the two different incubation temperatures. As expected with the use of a tetanus toxin-like ligand, N18-RE-105 cells not incubated with pronase had approximately equal amounts of cell-associated SOD:Tet451 regardless of incubation temperature (FIG. 4). However, while less than 15% of cell-associated hybrid protein was resistant to pronase treatment when cells were incubated at 0° C., greater than 90% of cell-associated SOD:Tet451 was pronase resistant after incubation at 37° C. When cells were incubated at 37° C. with hybrid protein in DMEM instead of binding buffer, there were considerable reductions in the levels of both total cell-associated and pronase resistant SOD:Tet451 (FIG. 5). Under these physiological conditions, only about ⅓ of cell-associated SOD:Tet451 was seen to be resistant to pronase digestion. Thus, while the overall efficiency of hybrid protein uptake appears to be diminished under physiological conditions, it is nonetheless apparent that SOD:Tet451 is readily internalized into N18-RE-105 cells.

The cellular uptake and persistence of SOD:Tet451 under physiological conditions was examined in N18-RE-105 cells which were pulse-loaded with hybrid protein and chased in DMEM. The results of this experiment show a relatively rapid loss of total cell-associated SOD:Tet451 over the first four hours, followed by a much more gradual loss over the next 20 hours (FIG. 5). The majority of the early loss of cell-associated hybrid protein appeared to be from the non-internalized (pronase sensitive) compartment. During this early phase, levels of pronase-sensitive SOD:Tet451 declined to 13% of the levels initially present at time zero, whereas levels of internalized hybrid protein were only reduced to 30% of their initial value. The small amount of hybrid protein that remained associated with the cells after 24 hours appeared to be only in the internalized compartment.

To ascertain whether levels of cell-associated SOD:Tet451 as determined by EIA represent enzymatically active hybrid protein, we measured cell-associated SOD:Tet451 and total SOD activity in N18-RE-105 cells that had been incubated with a relatively high concentration of hybrid protein. As shown in Table 2, under conditions which optimize hybrid protein binding/internalization, cells treated with 25 μg/ml SOD:Tet451 showed a modest elevation of total SOD activity relative to untreated controls. Statistical analysis of the enzyme activity results by one-way analysis of variance was unable to demonstrate a significant treatment effect for these small groups (n=4) at the level of $\alpha=0.05$ (df=2, F=4.13, p.=0.053). The incremental increase in SOD activity (~0.4 μg SOD/ml protein) detected following SOD:Tet451 incubation appeared consistent with the amounts of cell-associated hybrid protein as measured by EIA, adjusting for the molar specific activity of the hybrid protein and the partial purity of the affinity purified sample.

Table 2 shows data on the relationship of cell-associated SOD:Tet451 to total SOD activity in N18-RE-105 cells. Cells were incubated with 25 μg/ml SOD:Tet451 in binding buffer for one hour at 37° C. Thereafter, half the cells were briefly treated with pronase. Cell-associated SOD:Tet451 was measured by EIA while total SOD enzyme activity was determined by extrapolation from a human SOD-1 standard curve. Results are means±S.E.M. of 4 replicates for each treatment.

TABLE 2

| Treatment | Cell-associated hSOD-1 or SOD-Tet451 (pmoles/mg protein)[1] | Cell-associated hSOD-1 (per cent of total)[2] |
|---|---|---|
| hSOD-1 (1.86 μM) | 0.37 ± 0.028 | 0.0055 |
| SOD:Tet451 (44 nN) | 8.5 ± 1.4 | 5.8 |

In Table 2, the cell-associated hSOD-1 and SOD-Tet451 (pmoles/mg protein) values represent the mean±S.E.M. of 3–4 determinations for each treatment. The values were estimated from a standard curve of that same protein, and is reported as pmoles monomer/mg total cell protein. The cell-associated hSOD-1 (percent of total) values in Table 2 were obtained by dividing the average moles of cell-associated ligand per well by total moles of ligand initially present in the incubation medium.

Figure 6:
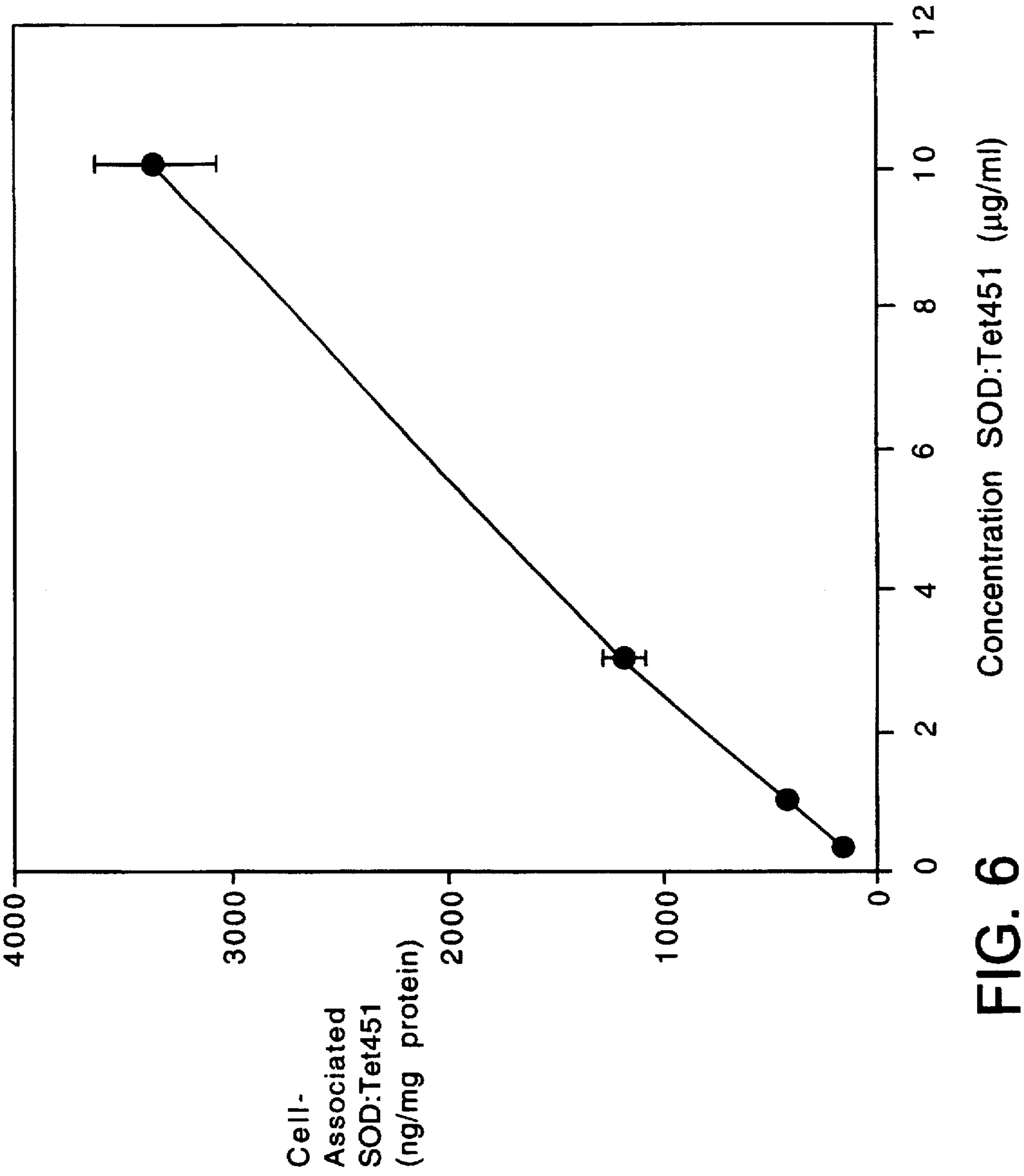
FIG. 6 is a dose-response curve for SOD:Tet451 association with cultured hippocampal neurons. Hippocampal cultures (10 days in vitro) were incubated with various concentrations of SOD:Tet451 in DMEM for one hour at 37° C. Cell lysates were analyzed for cell-associated SOD:Tet451 by an EIA specific for human SOD-1. Results are means±S.E.M. of 4 or 5 replicates for each treatment.

Because the N18-RE-105 cell line has certain characteristics which are not typical of mammalian nerve cells, we confirmed the neurotropic property of SOD:Tet451 by demonstrating its binding to cultured embryonic rat hippocampal neurons. Similar to our findings with the neuronal cell line, the association of hybrid protein with hippocampal cultures appeared to be dose-dependent and linear over the concentration range examined (FIG. 6). The primary neuron cultures also showed higher levels of cell-associated SOD:Tet451 when compared to N18-RE-105 cells. This result is consistent with an earlier study of tetanus toxin binding which showed that the toxin binding capacity of synaptic membrane preparations from rat brain was almost 3-fold greater than microsomal fractions from N18-RE-105 cells (Staub et al. (1986) *J. Neurosci.* 6: 1443–1451).

Finally, the efficiency of the hybrid protein in raising levels of cell-associated human SOD-1 in hippocampal cultures was directly compared to that of native human SOD-1. The hybrid protein was far superior to the native enzyme in delivering the SOD-1 moiety to cultured neurons. While our previous experiments have expressed cell-associated hybrid protein in units of ng SOD:Tet451/mg cell protein, the expression of cell-associated ligand on the basis of mol/mg protein was more appropriate for this comparison study given the >4-fold difference in molecular weight of the two ligands. As shown in Table 3, the efficacy of SOD:Tet451 for delivering human SOD-1 to hippocampal neurons from the incubation media was at least 1000-fold greater on a molar basis compared to the native form of the enzyme. During this relatively brief (1 hour) exposure, a substantial fraction (approximately 6%) of the total hybrid protein initially present in the incubation media was delivered to the hippocampal neurons.

Table 3 shows data on the association of native human SOD-1 or SOD:Tet451 with cultured hippocampal neurons. Hippocampal cultures (8 days In vitro) were incubated with either human SOD-1 or SOD:Tet451 in DMEM for 1 hour at 37° C. Cell lysates were analyzed for cell-associated hybrid protein by enzyme immunoassay for human SOD-1.

TABLE 3

| Treatment | Cell-associated SOD:Tet451 (μg/mg protein) | Total SOD activity (μg SOD/mg protein) |
|---|---|---|
| Control | — | 2.1 = 0.15 |
| SOD:Tet451 (25 μg/ml) | 5.0 ± 0.29 | 2.5 ± 0.11 |
| SOD:Tet451 (25 μg/ml) pronase) | 4.5 ± 0.22 | 2.5 ± 0.11 |

In Vivo Uptake and Transport of SOD-1/TTC Hybrid Protein

Specific uptake and transport of SOD:Tet451 by motor neurons has been demonstrated in mice. The tongues of adult C57/B16 mice were injected with either SOD:Tet451 (17 mg/ml, 10 μl total injection volume) or human SOD-1 (4 mg/ml, 10 μl total injection volume). Twenty-four hours after the injections, thin sections of the brainstem containing the cell bodies of the tongue motor neurons (i.e., the hypoglossal nucleus) were studied for evidence of SOD:Tet451 or human SOD-1, using immunostaining with monoclonal antibodies against TTC or SOD-1. The anti-SOD-1 monoclonal antibodies were specific for human SOD-1. Animals injected with SOD:Tet451 displayed immunoreactivity over the hypoglossal motor neurons and their processes, with either the anti-SOD-1 antibodies or the anti-TTC antibodies. No immuno-reactivity was observed in the control animals injected with the human SOD-1. As a control for the adequacy of the injection, SOD-1 was co-injected with the fluorescent dye Fluorogold (4%), which was transported to the motor neurons, where it was visualized using immunofluorescence. These experiments confirm that the SOD-1/TTC hybrid protein undergoes retrograde transport to the cell bodies of motor neurons, and that the observed transport is TTC-dependent.

Post Ischemic Infusion of SOD:Tet451

Drug preparation. SOD:Tet451 was prepared by ammonium sulfate precipitation and immunoaffinity chromatography of soluble bacterial protein obtained from sonicated lysates. Immunoaffinity columns were constructed by immobilizing anti-human SOD-1 monoclonal antibody (Sigma Chemical, St. Louis Mo.) on Protein-G Sepharose (Pharmacid Biotech, Piscataway, N.J.) according to manufacturer's instructions. Eluted column fractions were concentrated/buffer exchanged into phosphate-buffered saline using Centricon-50 filters (Amicon, Beverly, Mass.). General purity of affinity-purified SOD:Tet451 was qualitatively assessed by Coomassie blue staining of sodium dodecylsulfate-polyacrylamide gels. SOD-1 activity of native human SOD-1 (Sigma) and SOD:Tet451 was determined by inhibition of superoxide-mediated nitroblue tetrazolium reduction. Prior to administration to rats, proteins were filtered-sterilized and diluted in saline to obtain equivalent enzyme activity doses.

Animal surgery. Focal ischemic infarcts were produced in rats in accordance with institutional guidelines. Male Wistar rats (250–310g, Charles River Laboratories) were anesthetized with chloral hydrate prior to surgery. Rectal temperature was maintained at 37°±0.5° C. using a heating blanket connected to a temperature feedback monitor. The right femoral artery was cannulated with a silicon catheter for measurement of blood pressure and blood gases, and to obtain samples for determination of human SOD-1 levels in serum. The right femoral vein was similarly cannulated for infusions.

For ischemia surgery, a 4-0 nylon suture with a flame-rounded tip was inserted into the right external carotid artery just distal to the right common carotid bifurcation and advanced 18.5–19.5 mm (depending on the animal's weight) through the internal/intracranial carotid arteries until the tip occluded the origin of the MCA. The suture was left in place for 2 hours and then withdrawn into the external carotid artery. Immediately following restoration of bloodflow, animals were continuously infused for 3 hours with either saline (0.5 ml/hr), human SOD-1 (Sigma; 400 units/0.5 ml/hr at approximately 140 μg protein/ml), or SOD:Tet451 (400 units/0.5 ml/hr at approximately 0.5–0.8 mg total protein/ml). Arterial blood gases, pH, and hematocrit were monitored before vascular occlusion and at the end of drug the drug infusion. Mean arterial blood pressure was measured before and during occlusion and throughout drug infusion. Blood samples for determination of serum hSOD-1 levels were drawn 2.5 hours after the start of drug infusion and 30 minutes following drug termination.

Infarct measurement. Rats were sacrificed 48 hours after the onset of occlusion and cerebral infarct volume was determined by computer image analysis of coronal brain slices stained with 2% 2,3,5-triphenyltetrazolium chloride (Bioquant, R+M Biometrics, Nashville, Tenn.). Infarct volume was calculated using the "indirect" method, in which the infarcted area of a brain slice is first determined by subtracting the undamaged area of ipsilateral hemisphere from the total area of the contralateral hemisphere (Swanson et al., *J. Cereb. Blood Flow Metab.* 10: 290–293 (1990)). The infarcted area was then multiplied by section thickness (2 mm) to obtain infarct volume for that slice. Total brain infarct volume was finally obtained by summing the volumes of the series of 7 brain slices prepared from each animal. Statistical analysis of treatment groups was performed using one-way ANOVA followed by a two-tailed unpaired t-test.

Enzyme immunoassay (EIA). Human SOD-1 levels in rat serum were measured by EIA (Francis et al., *J. Biol. Chem.* 270: 15434–15442). ELISA plates (96-well) were precoated with sheep polyclonal anti-hSOD-1 total IgG (The Binding Site, San Diego, Calif.; 0.1 ml, 100 μg/ml in 0.1 M NaCarbonate, pH 9.6). After blocking the plate with 1% bovine serum albumin, 50 μl of mouse monoclonal anti-SOD-1 antibody (Sigman, 1:2000 dilution) was added along with 50 μl of diluted rat serum of 50 μl of human SOD-1 (0.4–6.4 ng/ml final concentration). The antibody/antigen mixture was incubated for 3 hours at room temperature and bound mouse antibody was detected with 0.1 ml/well alkaline phosphatase-conjugated goat anti-mouse IgG (Boehringer Mannheim, Indianapolis, Ind.; 1:2000 dilution). The alkaline phosphatase reaction was initiated by adding 0.2 ml/well of 4-nitrophenyl phosphate (1 mg/ml in 10 mM diethanolamine, pH 9.5). After overnight incubation at room temperature, the absorbance at 405 nm was determined using a Bio-Tek microplate reader.

Immunohistochemistry. The distribution of hSOD-1 (human SOD-1), TTxC (neuronal binding fragment of tetanus toxin), and SOD:Tet451 in infarcted rat brain was examined by immunohistochemistry. For these studies, rats were infused with either hSOD-1 or SOD:Tet451 as described above, or commercial recombinant TTxC (Boehringer Mannheim; 125 μg/ml, 0.5 ml/hr for 3 hours). Immediately after the 3-hour drug infusion, rats were transcardially perfused with PBS followed by 4% paraformaldehyde/PBS. Free-floating vibratome sections (50 μm) were incubated overnight at 4° C. with either mouse monoclonal anti-hSOD-1 (Sigma, 1:1000) or mouse monoclonal anti-TTC (Boehringer Mannheim, 3 μg/ml) diluted in PBS/0.05% Triton X-100/2% normal horse serum. Subsequent incubations with biotinylated secondary antibody, avidin/biotin/peroxidase complex, and diaminobenzidine/$H_2O_2$ were carried out according to the manufacturer's instructions (Vector Laboratories, Burlingame, Calif.).

Cerebral Infarction Results

Figure 7:
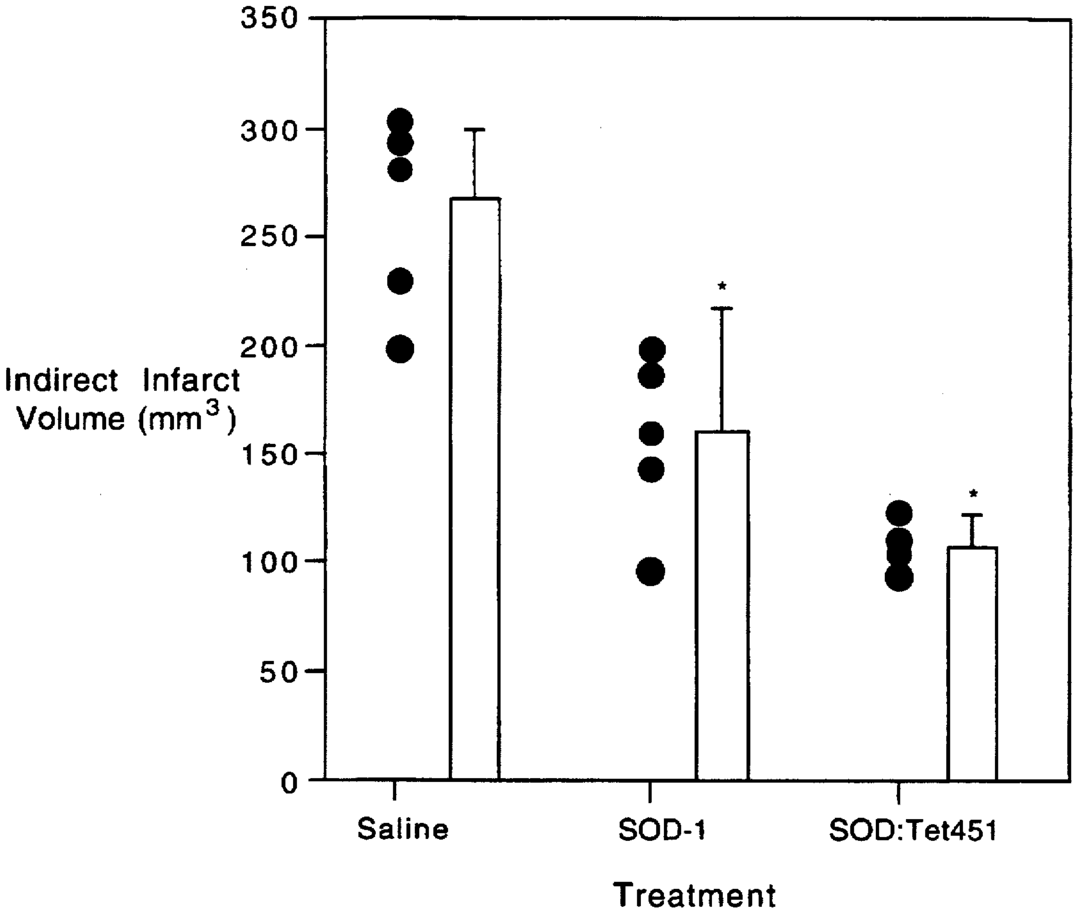
FIG. 7 is a scatter plot and bar graph of mean±S.D. infarct volume in brains of postischemic rats treated with saline (n=5), hSOD-1 (n=6), or SOD:Tet451 (n=5).

To assess the potential neuroprotective action of recombinant SOD:Tet451 in experimental brain ischemia/reperfusion, we intravenously infused rats with either saline, human SOD-1, or SOD:Tet451 immediately following the release of temporary (2 hr) unilateral MCA occlusion. FIG. 7 summarizes the effect of hSOD-1 or SOD:Tet451 treatment on cerebral infarct volume resulting from transient ischemia/reperfusion. When infused continuously for 3 hours after occlusion, both native hSOD-1 and SOD:Tet451 significantly reduced infarct volume as compared to saline-treated controls. Treatment with hSOD-1 was associated with a reduction to 57±16% of control while SOD:Tet451 treatment decreased infarct volume to 43±5% of the control value. Rats treated with hybrid protein showed a more consistent and greater reduction in infarct volume compared to animals treated with SOD-1; this difference was not statistically significant. A series of brain sections from one animal per treatment group was used in the estimation of infarct volume. Infarcts in vehicle-treated animals involve both cerebral cortex and underlying striatum. Treatments that reduce infarct size in this model typically spare the cortex. Accordingly, reductions in cerebral infarction associated with hSOD-1 or SOD:Tet451 treatment were seen predominantly in the cerebral cortex. None of the blood chemistry or hemodynamic measurements differed between the drug and saline-treated groups as determined by ANOVA (Tables 2 and 3).

TABLE 2

Blood Chemistry Measurements

| Blood Parameter | Saline (n = 5) Before Occlusion | Saline (n = 5) During Infusion | human SOD-1 (n = 6) Before Occlusion | human SOD-1 (n = 6) During Infusion | SOD:Tet451 (n = 5) Before Occlusion | SOD:Tet451 (n = 5) During Infusion |
|---|---|---|---|---|---|---|
| pH | 7.35 ± 0.04 | 7.36 ± 0.06 | 7.35 ± 0.02 | 7.39 ± 0.06 | 7.35 ± 0.02 | 7.47 ± 0.17 |
| $pCO_2$ | 42.8 ± 2.3 | 35.4 ± 3.4 | 45.4 ± 3.5 | 30.0 ± 10.3 | 43.9 ± 1.7 | 28.2 ± 3.8 |
| $pO_2$ | 83.3 ± 6.9 | 108 ± 27 | 87.7 ± 5.8 | 108 ± 27 | 86.5 ± 5.6 | 102 ± 16 |
| Hematocrit | 44.4 ± 1.5 | 47.0 ± 2.2 | 45.2 ± 3.2 | 47.5 ± 3.7 | 45.4 ± 3.2 | 47.0 ± 4.7 |

TABLE 3

| | Mean Arterial Blood Pressure | | | | |
|---|---|---|---|---|---|
| Treatment | Before Occlusion | During Occlusion | Before Infusion | During Infusion | End of Infusion |
| Saline | 76 ± 12.1 | 77.6 ± 12.6 | 80.0 ± 10.3 | 84.4 ± 14.4 | 110 ± 4.8 |
| Human SOD-1 | 89.7 ± 10.0 | 92.3 ± 13.8 | 96.0 ± 14.0 | 95.5 ± 9.6 | 108 ± 14.5 |
| SOD:Tet451 | 84.6 ± 6.4 | 93.2 ± 7.1 | 87.4 ± 16.7 | 90.6 ± 16.7 | 108 ± 16.4 |

Figure 8:
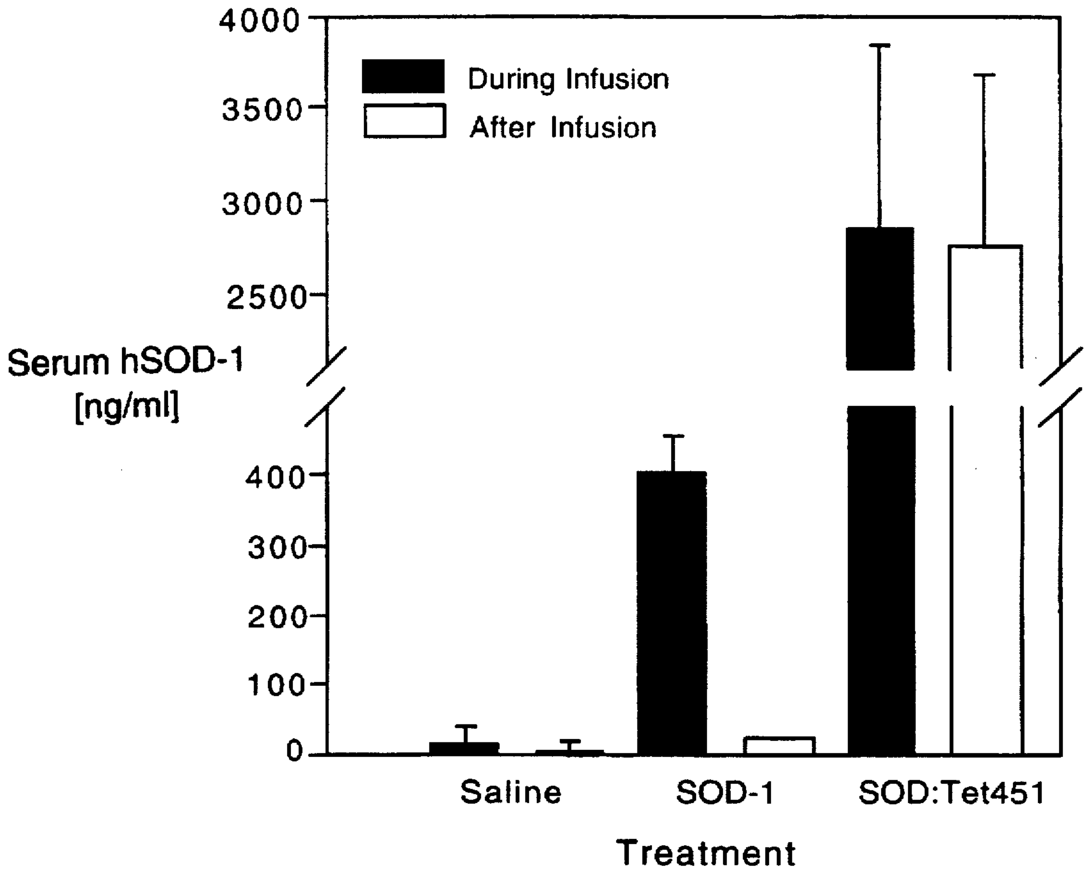
FIG. 8 is a bar graph of average serum hSOD-1 levels in postischemic rats during and after infusion with saline (n=3, x±S.D.), hSOD-1 (n=2, x±range), or SOD:Tet451 (n=3, x±S.D.). Serum hSOD-1 concentrations were determined by enzyme immunoassay of blood samples obtained after 2.5 hrs of drug infusion and also following 30 minutes of drug washout.

Augmenting the molecular weight of SOD-1 through various chemical modifications or recombinant fusion of SOD-1 monomers increases the serum half-life of the exogenous enzyme following iv administration in rats. Because the predicted molecular weight of SOD:Tet451 in homodimeric form is approximately 136 kd compared to 32 kd for the hSOD-1 homodimer, we hypothesized that the hybrid protein would possess a longer half-life in the bloodstream than the native SOD-1. To test this, we determined serum SOD1 levels in a small number of postischemic rats both during and shortly after drug infusion. As shown in FIG. 8, serum hSOD-1 levels in rats infused with SOD:Tet451 were at least 7-fold greater than hSOD-1 levels in animals given an equivalent activity of the native enzyme over the same time. Additionally, levels of hSOD-1 in serum samples obtained after 30 minutes of drug washout were markedly greater in animals receiving the hybrid protein. Serum hSOD-1 concentrations in SOD:Tet451-treated rats had declined, on average, less than 5% from the level measured during drug administration, while the decline in rats treated with native hSOD-1 was greater than 90%.

To determine whether SOD:Tet451 in the systemic circulation enters into focally ischemic brain tissue, we performed immunohistochemical studies on brain sections from a postischemic rat sacrificed immediately after infusion of the hybrid protein. Sections were also prepared from two ischemic animals which had received either free hSOD-1 or TTXC to serve as experimental controls. Brain sections from rats given hSOD-1 failed to show any immunoreactivity toward monoclonal anti-hSOD-1 antibody in either the ipsilateral or contralateral hemisphere. This particular anti-hSOD-1 antibody has previously been shown to selectively recognize hSOD-1 in formalin-fixed sections of mouse brain following retrograde axonal transport of SOD:Tet451 from a peripheral intramuscular injection site. In contrast, brain sections from a postischemic rat infused with TTXC revealed strong immunoreactivity toward anti-TTxC antibody localized to the ipsilateral striatum. This confirmed that blood-brain barrier disruption was present during the first three hours of reperfusion and more importantly that TTXC did indeed gain access to the affected CNS parenchyma from the systemic circulation. The pattern of striatal anti-TTxC immunoreactivity appeared heterogenous; staining was mostly concentrated in regions of interfascicular gray matter, a profile consistent with the selective binding of TTGXC to neuronal elements. Brain sections from a postischemic rat treated with SOD:Tet451 similarly showed strong anti-TTxC immunoreactivity over a substantial portion of the cerebral cortex ipsilateral to the vascular occlusion. Alternate sections from this same animal examined with anti-hSOD-1 antibody, in general, revealed a similar regional localization of immunoreactivity although the staining was less intense with the anti-SOD-1 antibody.

PROPHETIC EXAMPLES

The following prophetic examples are provided to illustrate the use of an SOD-1/TTC hybrid protein in the practice of this invention; they are not to be construed as limiting the scope of the invention in any way.

Case 1

Typically, a middle-aged or elderly man with familial amyotrophic lateral sclerosis (FALS) is treated with recombinant SOD:Tet451. At the time of treatment he typically will have had six months of progressive wasting and weakness of his arms. Electrophysiologic diagnostic studies typically would show evidence of widespread muscle denervation and normal sensory function. Erythrocyte SOD-1 levels will typically be below normal, e.g., 50% of normal. SOD:Tet451 is administered intravenously (e.g., 10 mg/ml in 100 ml of $D_5$ 0.5 normal saline) prepared from 1 gram of lyophilized protein. Intravenous treatments can be supplemented by intramuscular injection of SOD:Tet 451 (e.g., 50 mg/ml, 1cc) into the deltoid and biceps muscles bilaterally, as the most severely affected muscles. Treatments are repeated weekly, for a six month period. It is predicted that over that time isometric arm strength composite scores would increase significantly.

Case 2

Typically, a middle-aged to elderly woman with Parkinson's Disease is treated with SOD:Tet451. Such a patient might be also taking L-dopa (e.g., 1.2 grams/day) in combination with carbidopa and pergolide (e.g., 4 mg/day). She would typically have had her condition assessed with a Unified Parkinson's Disease Rating Scale ("UPDRS"). For such a patient, an omaya reservoir-shunt with in-line filter can be surgically placed into the lateral ventricles. SOD:Tet451 (e.g., 10 mg/ml, 10 ml in phosphate buffered saline) is instilled into the shunt by injection on a weekly basis). It is predicted that after six months of treatment the patient could be on a lower L-Dopa dosage, and display improved UPDRS motor scores. It is predicted that dyskinesia would no longer be present.

Case 3

Typically, a middle-aged man with Huntington's Disease is treated with SOD:Tet451. He would be expected to have a positive family history and positive genetic testing. Typically, over the past 2 years he would have had a decline in his full scale WAIS score (e.g., from 112 to 96). Typically, he would have a Total Functional Capacity score of about 8, and an AIMS score of about 12. For such a patient, an Omaya-reservoir-shunt with in-line filter can be surgically placed into the lateral ventricle. SOD:Tet451 (e.g., 10mg/ml, 10/ml in PBS) is instilled into the shunt on a weekly basis. After six months of treatment, it is predicted that the patient's WAIS, TFC, and AIMS scores would show significant improvement.

Case 4

Typically, an elderly woman seen emergently with the acute onset of a left hemiparesis is treated with SOD:Tet451.

With such a patient, SOD:Tet451 can be administered in the emergency room intravenously (e.g., 20/mg/ml, 100ml in $D_5$ 0.2 normal saline) after MRI scanning reveals abnormalities consistent with an infarction in the distribution of the right middle cerebral artery. SOD:Tet451 infusion is repeated on a daily basis for five days. At the time of discharge, 10 days after the cerebral vascular accident, the patient's average MRC motor score would be expected to have improved, and the patient would be expected to be ambulating up to 10 feet, with a walker. Six months later, the MRC score would be expected to show further improvement on the left, and it is predicted that the patient would be fully ambulatory, with a cane.

Other embodiments are within the following claims.

We claim:

1. A hybrid protein comprising:

(a) an enzymatically active Cu/Zn superoxide dismutase (SOD-1) moiety that retains enzymatic-activity following uptake of the hybrid protein into a neuron; and (b) a tetanus toxin fragment C (TTC) moiety capable of selectively delivering the hybrid protein into neurons.

2. The hybrid protein of claim 1, wherein said SOD-1 moiety is a human SOD-1 moiety.

3. The hybrid protein of claim 2, wherein said human SOD-1 moiety is a full length human SOD-1 polypeptide.

4. The hybrid protein of claim 1, wherein said TTC moiety consists of amino acid residues 856–1315 of the heavy chain of the tetanus holotoxin.

5. The hybrid protein of claim 1, wherein said enzymatic activity retained following uptake of the hybrid protein into a neuron is at least 50% of the maximum enzymatic activity displayed by an equivalent amount (on a molar basis) of non-fused SOD-1 consisting of the same amino acid sequence as the SOD-1 moiety of the hybrid protein.

6. The hybrid protein of claim 1, wherein said TTC moiety results in neuronal uptake of the hybrid protein that is at least 1,000-fold greater than neuronal uptake of a non-fused SOD-1 consisting of the same amino acid sequence as the SOD-1 moiety of the hybrid protein.

7. The hybrid protein of claim 1, wherein said hybrid protein consists of SEQ ID NO:5.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:1:

GGAATTCGTT TGCGTCGTAG TCTCCTGCA 29

( 2 ) INFORMATION FOR SEQ ID NO:2:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:2:

GGAATTCTTC TGACAAGTTT AATACCCAT 29

( 2 ) INFORMATION FOR SEQ ID NO:3:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:3:

GGGAATTCCA TATGGCGACG AAGG 24

( 2 ) INFORMATION FOR SEQ ID NO:4:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:4:

CGCGGATCCT TGGGCGATCC CAAT 24

( 2 ) INFORMATION FOR SEQ ID NO:5:

( i ) SEQUENCE CHARACTERISTICS:
( A ) LENGTH: 618 amino acids
( B ) TYPE: amino acid
( D ) TOPOLOGY: linear ( i i ) MOLECULE TYPE: protein ( x i ) SEQUENCE DESCRIPTION: SEQ ID NO:5:

Met Ala Thr Lys Ala Val Cys Val Leu Lys Gly Asp Gly Pro Val Gln
1 5 10 15

Gly Ile Ile Asn Phe Glu Gln Lys Glu Ser Asn Gly Pro Val Lys Val
20 25 30

Trp Gly Ser Ile Lys Gly Leu Thr Glu Gly Leu His Gly Phe His Val
35 40 45

His Glu Phe Gly Asp Asn Thr Ala Gly Cys Thr Ser Ala Gly Pro His
50 55 60

Phe Asn Pro Leu Ser Arg Lys His Gly Gly Pro Lys Asp Glu Glu Arg
65 70 75 80

His Val Gly Asp Leu Gly Asn Val Thr Ala Asp Lys Asp Gly Val Ala
85 90 95

Asp Val Ser Ile Glu Asp Ser Val Ile Ser Leu Ser Gly Asp His Cys
100 105 110

Ile Ile Gly Arg Thr Leu Val Val His Glu Lys Ala Asp Asp Leu Gly
115 120 125

Lys Gly Gly Asn Glu Glu Ser Thr Lys Thr Gly Asn Ala Gly Ser Arg
130 135 140

Leu Ala Cys Gly Val Ile Gly Ile Ala Gln Gly Ser Val Asp Ser Thr
145 150 155 160

Pro Leu Pro Phe Ser Tyr Ser Lys Asn Leu Asp Cys Trp Val Asp Asn
165 170 175

Glu Glu Asp Ile Asp Val Ile Leu Lys Lys Ser Thr Ile Leu Asn Leu
180 185 190

Asp Ile Asn Asn Asp Ile Ile Ser Asp Ile Ser Gly Phe Asn Ser Ser
195 200 205

Val Ile Thr Tyr Pro Asp Ala Gln Leu Val Pro Gly Ile Asn Gly Lys
210 215 220

Ala Ile His Leu Val Asn Asn Glu Ser Ser Glu Val Ile Val His Lys
225 230 235 240

Ala Met Asp Ile Glu Tyr Asn Asp Met Phe Asn Asn Phe Thr Val Ser
245 250 255

Phe Trp Leu Arg Val Pro Lys Val Ser Ala Ser His Leu Glu Gln Tyr
260 265 270

Gly Thr Asn Glu Tyr Ser Ile Ile Ser Ser Met Lys Lys His Ser Leu
275 280 285

Ser Ile Gly Ser Gly Trp Ser Val Ser Leu Lys Gly Asn Asn Leu Ile
290 295 300

Trp Thr Leu Lys Asp Ser Ala Gly Glu Val Arg Gln Ile Thr Phe Arg
305 310 315 320

Asp Leu Pro Asp Lys Phe Asn Ala Tyr Leu Ala Asn Lys Trp Val Phe
325 330 335

Ile Thr Ile Thr Asn Asp Arg Leu Ser Ser Ala Asn Leu Tyr Ile Asn
340 345 350

Gly Val Leu Met Gly Ser Ala Glu Ile Thr Gly Leu Gly Ala Ile Arg
355 360 365

Glu Asp Asn Asn Ile Thr Leu Lys Leu Asp Arg Cys Asn Asn Asn Asn
370 375 380

-continued

Gln Tyr Val Ser Ile Asp Lys Phe Arg Ile Phe Cys Lys Ala Leu Asn
385 390 395 400

Pro Lys Glu Ile Glu Lys Leu Tyr Thr Ser Tyr Leu Ser Ile Thr Phe
405 410 415

Leu Arg Asp Phe Trp Gly Asn Pro Leu Arg Tyr Asp Thr Glu Tyr Tyr
420 425 430

Leu Ile Pro Val Ala Ser Ser Ser Lys Asp Val Gln Leu Lys Asn Ile
435 440 445

Thr Asp Tyr Met Tyr Leu Thr Asn Ala Pro Ser Tyr Thr Asn Gly Lys
450 455 460

Leu Asn Ile Tyr Tyr Arg Arg Leu Tyr Asn Gly Leu Lys Phe Ile Ile
465 470 475 480

Lys Arg Tyr Thr Pro Asn Asn Glu Ile Asp Ser Phe Val Lys Ser Gly
485 490 495

Asp Phe Ile Lys Leu Tyr Val Ser Tyr Asn Asn Asn Glu His Ile Val
500 505 510

Gly Tyr Pro Lys Asp Gly Asn Ala Phe Asn Asn Leu Asp Arg Ile Leu
515 520 525

Arg Val Gly Tyr Asn Ala Pro Gly Ile Pro Leu Tyr Lys Lys Met Glu
530 535 540

Ala Val Lys Leu Arg Asp Leu Lys Thr Tyr Ser Val Gln Leu Lys Leu
545 550 555 560

Tyr Asp Asp Lys Asn Ala Ser Leu Gly Leu Val Gly Thr His Asn Gly
565 570 575

Gln Ile Gly Asn Asp Pro Asn Arg Asp Ile Leu Ile Ala Ser Asn Trp
580 585 590

Tyr Phe Asn His Leu Lys Asp Lys Ile Leu Gly Cys Asp Trp Tyr Phe
595 600 605

Val Pro Thr Asp Glu Gly Trp Thr Asn Asp
610 615

( 2 ) INFORMATION FOR SEQ ID NO:6:

( i ) SEQUENCE CHARACTERISTICS:
( A ) LENGTH: 1858 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:6:

AATGGCGACG AAGGCCGTGT GCGTGCTGAA GGGCGACGGC CCAGTGCAGG GCATCATCAA 60

TTTCGAGCAG AAGGAAAGTA ATGGACCAGT GAAGGTGTGG GGAAGCATTA AAGGACTGAC 120

TGAAGGCCTG CATGGATTCC ATGTTCATGA GTTTGGAGAT AATACAGCAG GCTGTACCAG 180

TGCAGGTCCT CACTTTAATC CTCTATCCAG AAAACACGGT GGGCCAAAGG ATGAAGAGAG 240

GCATGTTGGA GACTTGGGCA ATGTGACTGC TGACAAAGAT GGTGTGGCCG ATGTGTCTAT 300

TGAAGATTCT GTGATCTCAC TCTCAGGAGA CCATTGCATC ATTGGCCGCA CACTGGTGGT 360

CCATGAAAAA GCAGATGACT TGGGCAAAGG TGGAAATGAA GAAAGTACAA AGACAGGAAA 420

CGCTGGAAGT CGTTTGGCTT GTGGTGTAAT TGGGATCGCC CAAGGATCCG TCGACTCAAC 480

ACCACTTCCA TTTTCTTATT CTAAAAATCT GGATTGTTGG GTTGATAATG AAGAAGATAT 540

AGATGTTATA TTAAAAAAGA GTACAATTTT AAATTTAGAT ATTAATAATG ATATTATATC 600

AGATATATCT GGGTTTAATT CATCTGTAAT AACATATCCA GATGCTCAAT TGGTGCCCGG 660

-continued

```
AATAAATGGC AAAGCAATAC ATTTAGTAAA CAATGAATCT TCTGAAGTTA TAGTGCATAA   720
AGCTATGGAT ATTGAATATA ATGATATGTT TAATAATTTT ACCGTTAGCT TTTGGTTGAG   780
GGTTCCTAAA GTATCTGCTA GTCATTTAGA ACAATATGGC ACAAATGAGT ATTCAATAAT   840
TAGCTCTATG AAAAAACATA GTCTATCAAT AGGATCTGGT TGGAGTGTAT CACTTAAAGG   900
TAATAACTTA ATATGGACTT TAAAAGATTC CGCGGGAGAA GTTAGACAAA TAACTTTTAG   960
GGATTTACCT GATAAATTTA ATGCTTATTT AGCAAATAAA TGGGTTTTTA TAACTATTAC  1020
TAATGATAGA TTATCTTCTG CTAATTTGTA TATAAATGGA GTACTTATGG GAAGTGCAGA  1080
AATTACTGGT TTAGGAGCTA TTAGAGAGGA TAATAATATA ACATTAAAAC TAGATAGATG  1140
TAATAATAAT AATCAATACG TTTCTATTGA TAAATTTAGG ATATTTTGCA AAGCATTAAA  1200
TCCAAAAGAG ATTGAAAAAT TATACACAAG TTATTTATCT ATAACCTTTT TAAGAGACTT  1260
CTGGGGAAAC CCTTTACGAT ATGATACAGA ATATTATTTA ATACCAGTAG CTTCTAGTTC  1320
TAAAGATGTT CAATTGAAAA ATATAACAGA TTATATGTAT TTGACAAATG CGCCATCGTA  1380
TACTAACGGA AAATTGAATA TATATTATAG AAGGTTATAT AATGGACTAA AATTTATTAT  1440
AAAAAGATAT ACACCTAATA ATGAAATAGA TTCTTTTGTT AAATCAGGTG ATTTTATTAA  1500
ATTATATGTA TCATATAACA ATAATGAGCA CATTGTAGGT TATCCGAAAG ATGGAAATGC  1560
CTTTAATAAT CTTGATAGAA TTCTAAGAGT AGGTTATAAT GCCCCAGGTA TCCCTCTTTA  1620
TAAAAAAATG GAAGCAGTAA AATTGCGTGA TTTAAAAACC TATTCTGTAC AACTTAAATT  1680
ATATGATGAT AAAAATGCAT CTTTAGGACT AGTAGGTACC CATAATGGTC AAATAGGCAA  1740
CGATCCAAAT AGGGATATAT TAATTGCAAG CAACTGGTAC TTTAATCATT TAAAAGATAA  1800
AATTTTAGGA TGTGATTGGT ACTTTGTACC TACAGATGAA GGATGGACAA ATGATTAA    1858
```